United States Patent
Phan et al.

(10) Patent No.: US 9,855,701 B2
(45) Date of Patent: *Jan. 2, 2018

(54) SYSTEMS AND METHODS FOR VARYING ELASTIC MODULUS APPLIANCES

(71) Applicant: ALIGN TECHNOLOGY, INC., San Jose, CA (US)

(72) Inventors: Loc X. Phan, San Jose, CA (US); Muhammad Chishti, Washington, DC (US); Ross J. Miller, Sunnyvale, CA (US); H. Robert Vandenberg, San Ramon, CA (US); Eric Kuo, Foster City, CA (US)

(73) Assignee: ALIGN TECHNOLOGY, INC., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/139,796

(22) Filed: Apr. 27, 2016

(65) Prior Publication Data

US 2016/0236398 A1    Aug. 18, 2016

Related U.S. Application Data

(60) Continuation of application No. 14/298,030, filed on Jun. 6, 2014, now Pat. No. 9,351,809, which is a
(Continued)

(51) Int. Cl.
*A61C 3/00* (2006.01)
*B29C 51/00* (2006.01)
(Continued)

(52) U.S. Cl.
CPC .............. *B29C 51/002* (2013.01); *A61C 7/00* (2013.01); *A61C 7/08* (2013.01); *A61C 7/36* (2013.01);
(Continued)

(58) Field of Classification Search
CPC .... A61C 7/00; A61C 7/08; A61C 7/36; A61C 19/00; A61C 7/002; B29C 51/002;
(Continued)

(56) References Cited

U.S. PATENT DOCUMENTS

| | | |
|---|---|---|
| 2,467,432 A | 4/1949 | Kesling |
| 3,089,487 A | 5/1963 | Enicks et al. |

(Continued)

FOREIGN PATENT DOCUMENTS

| | | |
|---|---|---|
| AU | 3031677 A | 5/1979 |
| AU | 517102 B2 | 7/1981 |

(Continued)

OTHER PUBLICATIONS

AADR. American Association for Dental Research, Summary of Activities, Mar. 20-23, 1980, Los Angeles, CA, p. 195.
(Continued)

*Primary Examiner* — Heidi M Eide
(74) *Attorney, Agent, or Firm* — Wilson Sonsini Goodrich & Rosati

(57) ABSTRACT

The present invention provides improved devices, systems and methods for repositioning teeth from an initial tooth arrangement to a final tooth arrangement. Repositioning is accomplished with a system comprising a series of polymeric shell appliances configured to receive the teeth and incrementally reposition individual teeth in a series of successive steps. The individual appliances may be formed from layers having different stiffnesses (elastic moduluses), and the stiffnesses of successive appliances may be different, or both.

18 Claims, 12 Drawing Sheets

Related U.S. Application Data division of application No. 13/245,574, filed on Sep. 26, 2011, now Pat. No. 8,858,226, which is a continuation of application No. 11/227,810, filed on Sep. 14, 2005, now Pat. No. 8,235,713, which is a continuation of application No. 10/206,873, filed on Jul. 26, 2002, now Pat. No. 6,964,564, which is a continuation of application No. 09/874,724, filed on Jun. 4, 2001, now Pat. No. 6,454,565, which is a continuation-in-part of application No. 09/616,830, filed on Jul. 14, 2000, now Pat. No. 6,524,101.

(60) Provisional application No. 60/199,650, filed on Apr. 25, 2000, provisional application No. 60/199,649, filed on Apr. 25, 2000.

(51) Int. Cl.

| | | |
|---|---|---|
| A61C 7/00 | (2006.01) | |
| A61C 7/08 | (2006.01) | |
| A61C 7/36 | (2006.01) | |
| A61C 19/00 | (2006.01) | |
| B29C 47/02 | (2006.01) | |
| B29K 105/00 | (2006.01) | |
| B29L 9/00 | (2006.01) | |
| B29L 31/00 | (2006.01) | |

(52) U.S. Cl.
CPC ............ *A61C 19/00* (2013.01); *B29C 47/025* (2013.01); *A61C 7/002* (2013.01); *B29K 2105/256* (2013.01); *B29K 2995/0082* (2013.01); *B29L 2009/00* (2013.01); *B29L 2031/753* (2013.01)

(58) Field of Classification Search
CPC ...... B29K 2105/256; B29K 2995/0082; B29L 2009/00; B29L 2031/753
See application file for complete search history.

(56) References Cited

U.S. PATENT DOCUMENTS

| | | |
|---|---|---|
| 3,211,143 A | 10/1965 | Grossberg |
| 3,303,844 A | 2/1967 | Johnson et al. |
| 3,311,977 A | 4/1967 | Drake |
| 3,407,500 A | 10/1968 | Kesling |
| 3,600,808 A | 8/1971 | Reeve |
| 3,660,900 A | 5/1972 | Andrews |
| 3,683,502 A | 8/1972 | Wallshein |
| 3,738,005 A | 6/1973 | Cohen |
| 3,860,803 A | 1/1975 | Levine |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,055,895 A | 11/1977 | Huge |
| 4,195,046 A | 3/1980 | Kesling |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,370,129 A | 1/1983 | Huge |
| 4,448,735 A | 5/1984 | Huge |
| 4,478,580 A | 10/1984 | Barrut |
| 4,500,294 A | 2/1985 | Lewis |
| 4,504,225 A | 3/1985 | Yoshii |
| 4,505,673 A | 3/1985 | Yoshii |
| 4,526,540 A | 7/1985 | Dellinger |
| 4,551,096 A * | 11/1985 | Dellinger ............... A61C 7/146 433/24 |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,799,884 A | 1/1989 | Bergersen |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | van der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A * | 10/1991 | Abbatte ................ A61C 7/146 433/24 |
| 5,059,118 A | 10/1991 | Breads et al. |
| 5,100,316 A | 3/1992 | Wildman |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,184,306 A | 2/1993 | Erdman et al. |
| 5,186,623 A | 2/1993 | Breads et al. |
| 5,203,695 A | 4/1993 | Bergersen |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,431,562 A | 11/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,562,448 A | 10/1996 | Mushabac |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre |
| 5,621,648 A | 4/1997 | Crump |

(56) References Cited

U.S. PATENT DOCUMENTS

| | | | |
|---|---|---|---|
| 5,645,420 A | 7/1997 | Bergersen |
| 5,645,421 A | 7/1997 | Slootsky |
| 5,655,653 A | 8/1997 | Chester |
| 5,683,243 A | 11/1997 | Andreiko et al. |
| 5,692,894 A | 12/1997 | Schwartz et al. |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,742,700 A | 4/1998 | Yoon et al. |
| 5,746,221 A | 5/1998 | Jones et al. |
| 5,799,100 A | 8/1998 | Clarke et al. |
| 5,800,174 A | 9/1998 | Andersson |
| 5,823,778 A | 10/1998 | Schmitt et al. |
| 5,848,115 A | 12/1998 | Little et al. |
| 5,857,853 A | 1/1999 | van Nifterick et al. |
| 5,865,619 A | 2/1999 | Cross et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,934,288 A | 8/1999 | Avila et al. |
| 5,947,724 A | 9/1999 | Frantz et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 6,015,289 A | 1/2000 | Andreiko et al. |
| 6,044,309 A | 3/2000 | Honda |
| 6,049,743 A | 4/2000 | Baba |
| 6,062,861 A | 5/2000 | Andersson |
| 6,068,482 A | 5/2000 | Snow |
| 6,099,314 A | 8/2000 | Kopelman et al. |
| 6,123,544 A | 9/2000 | Cleary |
| 6,152,731 A | 11/2000 | Jordon et al. |
| 6,171,107 B1 | 1/2001 | Milne |
| 6,183,248 B1 | 2/2001 | Chishti et al. |
| 6,190,165 B1 | 2/2001 | Andreiko et al. |
| 6,217,325 B1 | 4/2001 | Chishti et al. |
| 6,217,334 B1 | 4/2001 | Hultgren |
| 6,244,861 B1 | 6/2001 | Andreiko et al. |
| 6,309,215 B1 | 10/2001 | Phan et al. |
| 6,315,553 B1 | 11/2001 | Sachdeva et al. |
| 6,322,359 B1 | 11/2001 | Jordan et al. |
| 6,350,120 B1 | 2/2002 | Sachdeva et al. |
| 6,382,975 B1 | 5/2002 | Poirier |
| 6,398,548 B1 | 6/2002 | Muhammad et al. |
| 6,402,707 B1 | 6/2002 | Ernst |
| 6,454,565 B2 | 9/2002 | Phan et al. |
| 6,482,298 B1 | 11/2002 | Bhatnagar |
| 6,524,101 B1 | 2/2003 | Phan et al. |
| 6,540,167 B2 | 4/2003 | Sasaki et al. |
| 6,554,611 B2 | 4/2003 | Chishti et al. |
| 6,572,372 B1 | 6/2003 | Phan et al. |
| 6,629,840 B2 | 10/2003 | Chishti et al. |
| 6,705,863 B2 | 3/2004 | Phan et al. |
| 6,722,880 B2 | 4/2004 | Chishti et al. |
| 6,964,564 B2 | 11/2005 | Phan et al. |
| 8,235,713 B2 | 8/2012 | Phan et al. |
| 8,858,226 B2 | 10/2014 | Phan et al. |
| 9,351,809 B2 | 5/2016 | Phan et al. |
| 2002/0006597 A1 | 1/2002 | Andreiko et al. |
| 2003/0009252 A1 | 1/2003 | Pavlovskaia et al. |
| 2003/0139834 A1 | 7/2003 | Nikolskiy et al. |
| 2003/0224311 A1 | 12/2003 | Cronauer |
| 2004/0128010 A1 | 7/2004 | Pavlovskaia et al. |
| 2005/0055118 A1 | 3/2005 | Nikolskiy et al. |
| 2012/0015314 A1 | 1/2012 | Phan et al. |
| 2014/0349242 A1 | 11/2014 | Phan et al. |

FOREIGN PATENT DOCUMENTS

| | | |
|---|---|---|
| AU | 5598894 A | 6/1994 |
| CA | 1121955 | 4/1982 |
| DE | 2749802 | 5/1978 |
| DE | 69327661 T | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 8/1995 |
| EP | 0731673 B1 | 9/1996 |
| EP | 0774933 B1 | 5/1997 |
| ES | 463897 | 1/1980 |
| FR | 2369828 A1 | 6/1978 |
| FR | 2652256 A1 | 3/1991 |
| GB | 15500777 | 8/1979 |
| JP | 53-058191 | 5/1978 |
| JP | 04-028359 | 1/1992 |
| JP | 08-508174 | 9/1996 |
| WO | WO 90/08512 A1 | 8/1990 |
| WO | WO 91/04713 A1 | 4/1991 |
| WO | WO 94/10935 A1 | 5/1994 |
| WO | WO 98/32394 A1 | 7/1998 |
| WO | WO 98/44865 A1 | 10/1998 |
| WO | WO 98/58596 A1 | 12/1998 |

OTHER PUBLICATIONS

Alcaniz, et aL, "An Advanced System for the Simulation and Planning of Orthodontic Treatments," Karl Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.

Alexander et al., "The DigiGraph Work Station Part 2 Clinical Management," JCO, pp. 402-407 (Jul. 1990).

Altschuler et al., "Analysis of 3-D Data for Comparative 3-D Serial Growth Pattern Studies of Oral-Facial Structures, " AADR Abstracts, Program and Abstracts of Papers, 57th General Session, IADR Annual Session, Mar. 29, 1979-Apr. 1, 1979, New Orleans Marriot, Journal of Dental Research, vol. 58, Jan. 1979, Special Issue A, p. 221.

Altschuler et al., "Laser Electro-Optic System for Rapid Three-Dimensional (3D) Topographic Mapping of Surfaces," Optical Engineering, 20(6):953-961 (1981).

Altschuler et al., "Measuring Surfaces Space-Coded by a Laser-Projected Dot Matrix," SPIE Imaging q Applications for Automated Industrial Inspection and Assembly, vol. 182, p. 187-191 (1979).

Altschuler, "3D Mapping of Maxillo-Facial Prosthesis," AADR Abstract #607, 2 pages total, (1980).

Andersson et al., "Clinical Results with Titanium Crowns Fabricated with Machine Duplication and Spark Erosion," Acta. Odontol. Scand., 47:279-286 (1989).

Andrews, The Six Keys to Optimal Occlusion Straight Wire, Chapter 3, pp. 13-24 (1989).

Bartels, et al., An Introduction to Splines for Use in Computer Graphics and Geometric Modeling, Morgan Kaufmann Publishers, pp. 422-425 (1987).

Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.

Baumrind et al., "Mapping the Skull in 3-D," reprinted from J. Calif. Dent. Assoc., 48(2), 11 pages total, (1972 Fall Issue).

Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of III., Aug. 26-30, 1975, pp. 142-166.

Baumrind, "Integrated Three-Dimensional Craniofacial Mapping: Background, Principles, and Perspectives," Semin. in Orthod., 7(4):223-232 (Dec. 2001).

Begole et al., "A Computer System for the Analysis of Dental Casts," The Angle Orthod., 51(3):253-259 (Jul. 1981).

Bernard et al.,"Computerized Diagnosis in Orthodontics for Epidemiological Studies: A ProgressReport," Abstract, J. Dental Res.

(56) References Cited

OTHER PUBLICATIONS

Special Issue, vol. 67, p. 169, paper presented at International Association for Dental Research 66th General Session, Mar. 9-13, 1988, Montreal, Canada.
Bhatia et al., "A Computer-Aided Design for Orthognathic Surgery," Br. J. Oral Maxillofac. Surg., 22:237-253 (1984).
Biggerstaff et al., "Computerized Analysis of Occlusion in the Postcanine Dentition," Am. J. Orthod., 61(3): 245-254 (Mar. 1972).
Biggerstaff, "Computerized Diagnostic Setups and Simulations," Angle Orthod., 40(1):28-36 (Jan. 1970).
Biostar Opeation & Training Manual. Great Lakes Orthodontics, Ltd. 199 Fire Tower Drive,Tonawanda, New York. 14150-5890, 20 pages total (1990).
Blu, et al., "Linear interpolation revitalized", IEEE Trans. Image Proc., 13(5):710-719 (May 2004).
Bourke, "Coordinate System Transformation," (Jun. 1996), p. 1, retrieved from the Internet Nov. 5, 2004, URL <http://astronomy.swin.edu.au/—pbourke/prolection/coords>.
Boyd et al., "Three Dimensional Diagnosis and Orthodontic Treatment of Complex Malocclusions With the Invisalipn Appliance," Semin. Orthod., 7(4):274-293 (Dec. 2001).
Brandestini et al., "Computer Machined Ceramic Inlays: In Vitro Marginal Adaptation," J. Dent. Res. Special Issue, Abstract 305, vol. 64, p. 208 (1985).
Brook et al., "An Image Analysis System for the Determination of Tooth Dimensions from Study Casts: Comparison with Manual Measurements of Mesio-distal Diameter," J. Dent. Res., 65(3):428-431 (Mar. 1986).
Burstone (interview), "Dr. Charles J. Burstone on the Uses of The Computer in Orthodontic Practice (Part 1)," J. Clin. Orthod., 13(7):442-453 (Jul. 1979).
Burstone (interview), "Dr. Charles J. Burstone on the Uses of The Computer in Orthodontic Practice (Part 2)," J. Clin. Orthod., 13(8):539-551 (Aug. 1979).
Burstone et al., Precision Adjustment of the Transpalatal Lingual Arch: Computer Arch Form Predetermination, Am, Journal of Orthodontics, vol. 79, No. 2 (Feb. 1981), pp. 115-133.
Cardinal Industrial Finishes, Powder Coatings information posted at <http://www.cardinalpaint.com> on Aug. 25, 2000, 2 pages.
Carnaghan, "An Alternative to Holograms for the Portrayal of Human Teeth," 4th Int'l. Conf. on Holographic Systems, Components and Applications, Sep. 15, 1993, pp. 228-231.
Chaconas et al., "The DigiGraph Work Station, Part 1, Basic Concepts," JCO, pp. 360-367 (Jun. 1990).
Chafetz et al., "Subsidence of the Femoral Prosthesis, A Stereophotogrammetric Evaluation," Clin. Orthop. Relat. Res., No. 201, pp. 60-67 (Dec. 1985).
Chiappone, (1980). Constructing the Gnathologic Setup and Positioner, J. Clin. Orthod, vol. 14, pp. 121-133.
Cottingham, (1969). Gnathologic Clear Plastic Positioner, Am. J. Orthod, vol. 55, pp. 23-31.
Crawford, "CAD/CAM in the Dental Office: Does It Work?", Canadian Dental Journal, vol. 57, No. 2, pp. 121-123 (Feb. 1991).
Crawford, "Computers in Dentistry: Part 1: CAD/CAM: The Computer Moves Chairside," "Part 2: F. Duret—A Man With a Vision," "Part 3: The Computer Gives New Vision-Literally," "Part 4: Bytes 'N Bites" The Computer Moves From the Front Desk to the Operatory, Canadian Dental Journal, vol. 54(9), pp. 661-666 (1988).
Crooks, "CAD/CAM Comes to USC," USC Dentistry, pp. 14-17 (Spring 1990).
Cureton, Correcting Malaligned Mandibular Incisors with Removable Retainers, J. Clin. Orthod, vol. 30, No. 7 (1996) pp. 390-395.
Curry et al., "Integrated Three-Dimensional Craniofacial Mapping at the Craniofacial Research Instrumentation Laboratory/University of the Pacific," Semin. Orthod., 7(4):258-265 (Dec. 2001).
Cutting et al., "Three-Dimensional Computer-Assisted Design of Craniofacial Surgical Procedures: Optimization and Interaction with Cephalometric and CT-Based Models," Plast. 77(6):877-885 (Jun. 1986).
DCS Dental AG, "The CAD/CAM 'DCS Titan System' for Production of Crowns/Bridges," DSC Production, pp. 1-7 (Jan. 1992.
Definition for gingiva. Dictionary.com p. 1-3. Retrieved from the internet Nov. 5, 2004 <http://reference.com/search/search?q=gingiva>.
DeFranco et al., "Three-Dimensional Large Displacement Analysis of Orthodontic Appliances," J. Biomechanics, 9:793-801 (1976).
Dental Institute University of Zurich Switzerland, Program for International Symposium on Computer Restorations: State of the Art of the CEREC-Method, May 1991, 2 pages total.
Dentrac Corporation, Dentrac document, pp. 4-13 (1992).
Dent-X posted on Sep. 24, 1998 at <http://www.dent-x.com/DentSim.htm>, 6 pages.
Doyle, "Digital Dentistry," Computer Graphics World, pp. 50-52, 54 (Oct. 2000).
DuraClearTM product information, Allesee Orthodontic Appliances—Pro Lab, 1 page (1997).
Duret et al, "CAD-CAM in Dentistry," J. Am. Dent. Assoc. 117:715-720 (Nov. 1988).
Duret et al., "CAD/CAM Imaging in Dentistry," Curr. Opin. Dent., 1:150-154 (1991).
Duret, "The Dental CAD/CAM, General Description of the Project," Hennson International Product Brochure, 18 pages total, Jan. 1986.
Duret,"Vers Une Prosthese Informatisee," (English translation attached), Tonus, vol. 75, pp. 55-57 (Nov. 15, 1985).
Economides, "The Microcomputer in the Orthodontic Office," JCO, pp. 767-772 (Nov. 1979).
Elsasser, Some Observations on the History and Uses of the Kesling Positioner, Am. J. Orthod. (1950) 36:368-374.
English translation of Japanese Laid-Open Publication No. 63-11148 to inventor T. Ozukuri (Laid-Open on Jan. 18, 1998) pp. 1-7.
Felton et al., "A Computerized Analysis of the Shape and Stability of Mandibular Arch Form," Am. J. Orthod. Dentofacial Orthop., 92(6):478-483 (Dec. 1987).
Friede et al., "Accuracy of Cephalometric Prediction in Orthognathic Surgery," Abstract of Papers, J. Dent. Res., 70:754-760 (1987).
Futterling et a/., "Automated Finite Element Modeling of a Human Mandible with Dental Implants," JS WSCG '98—Conference Program, retrieved from the Internet: <http://wscg.zcu.cz/wscg98/papers98/Strasser 98.pdf>, 8 pages.
Gao et al., "3-D element Generation for Multi-Connected Complex Dental and Mandibular Structure," Proc. Intl Workshop on Medical Imaging and Augmented Reality, pp. 267-271 (Jun. 12, 2001).
Gim-Alldent Deutschland, "Das DUX System: Die Technik," 2 pages total (2002).
Gottleib et al., "JCO Interviews Dr. James A. McNamura, Jr., on the Frankel Appliance: Part 2: Clinical 1-1 Management," J. Clin. Orthod., 16(6):390-407 (Jun. 1982).
Grayson, "New Methods for Three Dimensional Analysis of Craniofacial Deformity, Symposium: Computerized Facial Imaging in Oral and Maxiiofacial Surgery," AAOMS, 3 pages total, (Sep. 13, 1990).
Guess et al., "Computer Treatment Estimates in Orthodontics and Orthognathic Surgery," JCO, pp. 262-328 (Apr. 1989).
Heaven et al. "Computer-Based Image Analysis of Artificial Root Surface Caries," Abstracts of Papers, J. Dent. Res., 70:528 (Apr. 17-21, 1991).
Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingampproduction/november011996/simulatingstressputonfa . . . >.
Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total).

(56) References Cited

OTHER PUBLICATIONS

Hoffmann, et al., "Role of Cephalometry for Planning of Jaw Orthopedics and Jaw Surgery Procedures," (Article Summary in English, article in German), Informatbnen, pp. 375-396 (Mar. 1991).
Hojjatie et al., "Three-Dimensional Finite Element Analysis of Glass-Ceramic Dental Crowns," J. Biomech., 23(11):1157-1166 (1990).
Huckins, "CAD-CAM Generated Mandibular Model Prototype from MRI Data," AAOMS, p. 96 (1999).
Important Tip About Wearing the Red White & Blue Active Clear Retainer System, Allesee Orthodontic Appliances—Pro Lab, 1 page (1998).
JCO Interviews, Craig Andreiko, DDS, MS on the Elan and Orthos Systems, JCO, pp. 459-468 (Aug. 1994).
JCO Interviews, Dr. Homer W. Phillips on Computers in Orthodontic Practice, Part 2, JCO. 1997; 1983:819-831.
Jerrold, "The Problem, Electronic Data Transmission and the Law," AJO-DO, pp. 478-479 (Apr. 1988).
Jones et al., "An Assessment of the Fit of a Parabolic Curve to Pre- and Post-Treatment Dental Arches," Br. J. Orthod., 16:85-93 (1989).
JP Faber et al., "Computerized Interactive Orthodontic Treatment Planning," Am. J. Orthod., 73(1):36-46 (Jan. 1978).
Kamada et.al., Case Reports on Tooth Positioners Using LTV Vinyl Silicone Rubber, J. Nihon University School of Dentistry (1984) 26(1): 11-29.
Kamada et.al., Construction of Tooth Positioners with LTV Vinyl Silicone Rubber and Some Case KJ Reports, J. Nihon University School of Dentistry (1982) 24(1):1-27.
Kanazawa et al., "Three-Dimensional Measurements of the Occlusal Surfaces of Upper Molars in a Dutch Population," J. Dent Res., 63(11):1298-1301 (Nov. 1984).
Kesling et al., The Philosophy of the Tooth Positioning Appliance, American Journal of Orthodontics and Oral surgery. 1945; 31:297-304.
Kesling, Coordinating the Predetermined Pattern and Tooth Positioner with Conventional Treatment, Am. J. Orthod. Oral Surg. (1946) 32:285-293.
Kleeman et al., The Speed Positioner, J. Clin. Orthod. (1996) 30:673-680.
Kochanek, "Interpolating Splines with Local Tension, Continuity and Bias Control," Computer Graphics, 18(3):33-41 (Jul. 1984). Oral Surgery (1945) 31 :297-30.
Kunii et al., "Articulation Simulation for an Intelligent Dental Care System," Displays 15:181-188 (1994).
Kuroda et al., Three-Dimensional Dental Cast Analyzing System Using Laser Scanning, Am. J. Orthod. Dentofac. Orthop. (1996) 110:365-369.
Laminated. (n.d.). Dictionary.com Unabridged. Retrieved Apr. 28, 2010, from Dictionary.com website: http://dictionary.reference.com/browse/LAMINATED.
Laurendeau, et al., "A Computer-Vision Technique for the Acquisition and Processing of 3-D Profiles of 7 Dental Imprints: An Application in Orthodontics," IEEE Transactions on Medical Imaging, 10(3):453-461 (Sep. 1991).
Leinfelder, et al., "A New Method for Generating Ceramic Restorations: a CAD-CAM System," J. Am. 1-1 Dent. Assoc., 118(6):703-707 (Jun. 1989).
Manetti, et al., "Computer-Aided Cefalometry and New Mechanics in Orthodontics," (Article Summary in English, article in German), Fortschr Kieferorthop 44, 370-376 (Nr. 5), 1983.
McCann, "Inside the ADA," J. Amer. Dent. Assoc., 118:286-294 (Mar. 1989).
McNamara et al., "Invisible Retainers," J. Cfin. Orthod., pp. 570-578 (Aug. 1985).
McNamara et al., Orthodontic and Orthopedic Treatment in the Mixed Dentition, Needham Press, pp. 347-353 (Jan. 1993).
Moermann et al., "Computer Machined Adhesive Porcelain Inlays: Margin Adaptation after Fatigue Stress," IADR Abstract 339, J. Dent. Res., 66(a):763 (1987).

Moles, "Correcting Mild Malalignments—As Easy As One, Two, Three," AOA/Pro Corner, vol. 11, No. 1, 2 pages (2002).
Mormann et al., "Marginale Adaptation von adhasuven Porzellaninlays in vitro," Separatdruck aus:Schweiz. Mschr. Zahnmed. 95: 1118-1129, 1985.
Nahoum, "The Vacuum Formed Dental Contour Appliance," N. Y. State Dent. J., 30(9):385-390 (Nov. 1964).
NASH, "CEREC CAD/CAM Inlays: Aesthetics and Durability in a Single Appointment," Dent. Today, 9(8):20, 22-23 (Oct. 1990).
Nishiyama et al., "A New Construction of Tooth Repositioner by LTV Vinyl Silicone Rubber," J. Nihon Univ. Sch. Dent., 19(2):93-102 (1977).
Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.
Pinkham, "Foolish Concept Propels Technology," Dentist, 3 pages total, Jan./Feb. 1989.
Pinkham, "Inventor's CAD/CAM May Transform Dentistry," Dentist, 3 pages total, Sep. 1990.
Ponitz, "Invisible Retainers," Am. J. Orthod., 59(3):266-272 (Mar. 1971).
Procera Research Projects, "Procera Research Projects 1993—Abstract Collection," pp. 3-7 28 (1993).
Proffit et al., Contemporary Orthodontics, (Second Ed.), Chapter 15, Mosby Inc., pp. 470-533 (Oct. 1993).
Raintree Essix & ARS Materials, Inc., Raintree Essix, Technical Magazine, Table of contents and Essix Appliances, <http://www.essix.com/magazine/defaulthtml> Aug. 13, 1997.
Redmond et al., "Clinical Implications of Digital Orthodontics," Am. J. Orthod. Dentofacial Orthop., 117(2):240-242 (2000).
Rekow et al. "CAD/CAM for Dental Restorations—Some of the Curious Challenges," IEEE Trans. Biomed. Eng., 38(4):314-318 (Apr. 1991).
Rekow et al., "Comparison of Three Data Acquisition Techniques for 3-D Tooth Surface Mapping," Annual International Conference of the IEEE Engineering in Medicine and Biology Society, 13(1):344-345 1991.
Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).
Rekow, "CAD/CAM in Dentistry: A Historical Perspective and View of the Future," J. Can. Dent. Assoc., 58(4):283, 287-288 (Apr. 1992).
Rekow, "Computer-Aided Design and Manufacturing in Dentistry: A Review of the State of the Art," J. Prosthet. Dent., 58(4):512-516 (Oct. 1987).
Rekow, "Dental CAD-CAM Systems: What is the State of the Art?", J. Amer. Dent. Assoc., 122:43-48 1991.
Rekow, "Feasibility of an Automated System for Production of Dental Restorations, Ph.D. Thesis," Univ. of Minnesota, 244 pages total, Nov. 1988.
Richmond et al., "The Development of a 3D Cast Analysis System," Br. J. Orthod., 13(1):53-54 (Jan. 1986).
Richmond et al., "The Development of the PAR Index (Peer Assessment Rating): Reliability and Validity," Eur. J. Orthod., 14:125-139 (1992).
Richmond, "Recording the Dental Cast in Three Dimensions," Am. J. Orthod. Dentofacial Orthop., 92(3):199-206 (Sep. 1987).
Rudge, "Dental Arch Analysis: Arch Form, A Review of the Literature," Eur. J. Orthod., 3(4):279-284 1981.
Sakuda et al., "Integrated Information-Processing System in Clinical Orthodontics: An Approach with Use of a Computer Network System," Am. J. Orthod. Dentofacial Orthop., 101(3): 210-220 (Mar. 1992).
Schellhas et al., "Three-Dimensional Computed Tomography in Maxillofacial Surgical Planning," Arch. Otolamp!. Head Neck Surg., 114:438-442 (Apr. 1988).

(56) References Cited

OTHER PUBLICATIONS

Schroeder et al., Eds. The Visual Toolkit, Prentice Hall PTR, New Jersey (1998) Chapters 6, 8 & 9, (pp. 153-210,309-354, and 355-428, respectively).
Shilliday, (1971). Minimizing finishing problems with the mini-positioner, Am. J. Orthod. 59:596-599.
Siemens, "CEREC—Computer-Reconstruction," High Tech in der Zahnmedizin, 14 pages total (2004).
Sinclair, "The Readers' Corner," J. Clin. Orthod., 26(6):369-372 (Jun. 1992).
Sirona Dental Systems GmbH, CEREC 3D, Manuel utiiisateur, Version 2.0X (in French), 2003,114 pages total.
Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
The Choice is Clear: Red, White & Blue ... . The Simple, Affordable, No-Braces Treatment, Allesee Orthodontic Appliances-Pro Lab product information for doctors. http://ormco.com/aoa/appliances-services/RWB/doctorhtml>, 5 pages (May 19, 2003).
The Choice is Clear: Red, White & Blue . . . The Simple, Affordable, No-Braces Treatment, Allesee Orthodontic Appliances-Pro Lab product information for patients, <http://ormco.com/aoa/appliancesservices/RWB/patients.html>, 2 pages (May 19, 2003).
The Choice is Clear: Red, White & Blue . . . The Simple, Affordable, No-Braces Treatment, Allesee Orthodontic Appliances-Pro Lab product information, 6 pages (2003).
The Red, White & Blue Way to Improve Your Smile! Allesee Orthodontic Appliances—Pro Lab product information for patients, 2 pages 1992.
Truax L., "Truax Clasp-Less(TM) Appliance System," Funct. Orthod., 9(5):22-4, 26-8 (Sep.-Oct. 1992).
Tru-Tain Orthodontic & Dental Supplies, Product Brochure, Rochester, Minnesota 55902, 16 pages total (1996).
U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050,342, filed Jun. 20, 1997, 41 pages total.
Van Der Linden et al., "Three-Dimensional Analysis of Dental Casts by Means of the Optocom," J. Dent. Res., p. 1100 (Jul.-Aug. 1972).
Van Der Linden, "A New Method to Determine Tooth Positions and Dental Arch Dimensions," J. Dent. Res., 51(4):1104 (Jul.-Aug. 1972).
Van Der Zel, "Ceramic-Fused-to-Metal Restorations with a New CAD/CAM System," Quintessence Int., 24(11):769-778 (1993).
Varady et al., "Reverse Engineering of Geometric Models—An Introduction," Computer-Aided Design, 29(4):255-268,1997.
Verstreken et al., "An Image-Guided Planning System for Endosseous Oral Implants," IEEE Trans. Med. Imaging, 17(5):842-852 (Oct. 1998).
Warunek et al., Physical and Mechanical Properties of Elastomers in Orthodonic Positioners, Am J. Orthod. Dentofac. Orthop, vol. 95, No. 5, (May 1989) pp. 399-400.
Warunek et.al., Clinical Use of Silicone Elastomer Applicances, JCO (1989) XXIII(10):694-700.
Wells, Application of the Positioner Appliance in Orthodontic Treatment, Am. J. Orthodont. (1970) 58:351-366.
Williams, "Dentistry and CAD/CAM: Another French Revolution," J. Dent. Practice Admin., pp. 2-5 (Jan./Mar. 1987).
Williams, "The Switzerland and Minnesota Developments in CAD/CAM," J. Dent. Practice Admin., pp. 50-55 (Apr./Jun. 1987).
Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.
WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.
Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).
Yamamoto et al., "Optical Measurement of Dental Cast Profile and Application to Analysis of Three-Dimensional Tooth Movement in Orthodontics," Front. Med. Biol. Eng., 1(2):119-130 (1988).
Yamamoto et al., "Three-Dimensional Measurement of Dental Cast Profiles and Its Applications to Orthodontics," Conf. Proc. IEEE Eng. Med. Biol. Soc., 12(5):2051-2053 (1990).
Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.
Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).
Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).
Yoshii, "Research on a New Orthodontic Appliance: The Dynamic Positioner (D.P.); III.—The General Concept of the D.P. Method and Its Therapeutic Effect, Part 2. Skeletal Reversed Occlusion Case Reports," Nippon Dental Review, 458:112-129 (Dec. 1980).
Yoshii, "Research on a New Orthodontic Appliance: The Dynamic Positioner (D.P.); III. The General Concept of the D.P. Method and Its Therapeutic Effect, Part 1, Dental and Functional Reversed Occlusion Case Reports," Nippon Dental Review, 457:146-164 (Nov. 1980).
You May Be a Candidate for This Invisible No-Braces Treatment, Allesee Orthodontic Appliances—Pro Lab product information for patients, 2 pages (2002).

* cited by examiner

SYSTEMS AND METHODS FOR VARYING ELASTIC MODULUS APPLIANCES

CROSS-REFERENCES TO RELATED APPLICATIONS

This application is a continuation of U.S. patent application Ser. No. 14/298,030, filed Jun. 6, 2014, now U.S. Pat. No. 9,351,809, issued May 31, 2016, which is a divisional of U.S. patent application Ser. No. 13/245,574, filed Sep. 26, 2011, now U.S. Pat. No. 8,858,226, issued Oct. 14, 2014, which is a continuation of U.S. patent application Ser. No. 11/227,810, filed Sep. 14, 2005, now U.S. Pat. No. 8,235,713, issued Aug. 7, 2012, which is a continuation of U.S. patent application Ser. No. 10/206,873, filed Jul. 26, 2002, now U.S. Pat. No. 6,964,564, issued Nov. 15, 2005, which is a continuation of U.S. patent application Ser. No. 09/874,724, filed Jun. 4, 2001, now U.S. Pat. No. 6,454,565, issued Sep. 24, 2002, which is a continuation-in-part of U.S. patent application Ser. No. 09/616,830, filed Jul. 14, 2000, now U.S. Pat. No. 6,524,101, issued Feb. 25, 2003, which claims the benefit of U.S. Provisional Patent Application No. 60/199,650, filed Apr. 25, 2000, and U.S. Provisional Patent Application No. 60/199,649, filed Apr. 25, 2000, the full disclosures of which are incorporated herein by reference. The disclosure of this application is also related to U.S. patent application Ser. No. 09/616,222, filed Jul. 14, 2000, now U.S. Pat. No. 6,572,372, issued Jun. 3, 2003, the full disclosure of which is incorporated herein by reference.

BACKGROUND OF THE INVENTION

This invention relates in general to a method of repositioning teeth for use in orthodontic treatment. Particularly, this invention relates to the use of orthodontic appliances for producing tooth movements. More particularly, this invention relates to the use of a plurality of elastic repositioning appliances for producing such tooth movements.

Orthodontic treatments involve repositioning misaligned teeth and improving bite configurations for improved cosmetic appearance and dental function. Repositioning teeth is accomplished by applying controlled forces to the teeth over an extended period of time. This is conventionally accomplished by wearing what are commonly referred to as "braces." Braces comprise a variety of appliances such as brackets, bands, archwires, ligatures, and O-rings. After they are bonded to the teeth, periodic meetings with the orthodontist are required to adjust the braces. This involves installing different archwires having different force-inducing properties or by replacing or tightening existing ligatures. Between meetings, the patient may be required to wear supplementary appliances, such as elastic bands or headgear, to supply additional or extraoral forces.

Although conventional braces are effective, they are often a tedious and time consuming process requiring many visits to the orthodontists office. Moreover, from a patient's perspective, they are unsightly and uncomfortable. Consequently, alternative orthodontic treatments have developed. A particularly promising approach relies on the use of elastic positioning appliances for realigning teeth. Such appliances comprise a thin shell of elastic material that generally conforms to a patient's teeth but is slightly out of alignment with the initial tooth configuration. Placement of the elastic positioner over the teeth applies controlled forces in specific locations to gradually move the teeth into the new configuration. Repetition of this process with successive appliances comprising new configurations eventually moves the teeth through a series of intermediate configurations to a final desired configuration. A full description of an exemplary elastic polymeric positioning appliance is described in U.S. Pat. No. 5,975,893, and in published PCT application WO 98/58596 which designates the United States and which is assigned to the assignee of the present invention. Both documents are incorporated by reference for all purposes.

In addition to their ease of use, polymeric positioning appliances are generally transparent, providing an improved cosmetic appearance, and impart substantial force on the teeth, due to stiffness of the appliance. The stiffness of an elastic positioning appliance is a result of the modulus of the thermoformable polymer materials from which it is made. The higher the modulus of the materials, the higher the stiffness of the appliance. When a patient positions such an appliance over a prescribed group of teeth, one or more of the teeth will provide a base or anchor region for holding the positioning appliance in place while the stiffness of the polymeric material will impart a resilient repositioning force against one or a portion of the remaining teeth. However, the stiffer the appliance, the more difficult it is to slip the misaligned appliance over the teeth and fully engage the appropriate surfaces; the appliance often has the tendency to disengage or "pop off". Likewise, once it is firmly seated, it is more difficult to remove. Further, a stiff appliance is less forgiving in cases of lowered patient compliance. If a patient were to remove the appliance for an unprescribed period of treatment time, the patient's teeth may move slightly out of the planned tooth arrangement. When attempting to reapply the appliance, it may be too rigid to accommodate these slight differences and a new appliance may need to be created. Similarly, the tooth positions defined by the cavities in each successive appliance must not differ beyond a limiting dimension from those defined by the prior appliance or, again, it may be too rigid to accommodate the differences. Consequently, only small increments in tooth repositioning may be made with each appliance.

Thus, it would be desirable to provide tooth positioners, systems, and methods which apply adequate force to selected teeth yet overcome the inherent limitations of stiffness in the polymeric material. Likewise, it would be desirable to reduce the number of positioners required for a treatment plan by increasing the size of the repositioning increments throughout the plan. Further, it would be desirable to reduce the cost of lowered patient compliance by reducing the need for new appliances to be created for patient treatment resumption. At least some of these objectives will be met by the designs and methods of the present invention described hereinafter.

SUMMARY OF THE INVENTION

The present invention provides improved devices, systems and methods for repositioning teeth from an initial tooth arrangement to a final tooth arrangement. Repositioning is accomplished with a system comprising a series of polymeric appliances configured to receive the teeth in a cavity and incrementally reposition individual teeth in a series of successive steps. This is accomplished by applying force to specific surfaces of the teeth to cause directed movement. In order to apply such force, one or more of the teeth will provide a base or anchor region for holding the positioning appliance in place while the stiffness of the polymeric material will impart a resilient repositioning force against one or more of the remaining teeth. However, such stiffness creates limitations in ease of use, patient compliance, and overall cost in material, manufacturing labor and treatment time.

To overcome these limitations, the present invention utilizes polymeric or other material appliances with portions differing in rigidity, hardness, or stiffness. Portions of the appliance designed to apply specific forces may have different elastic moduluses (stiffnesses) and/or hardnesses than other portions. Alternatively, elastic moduluses and/or hardnesses may vary from one appliance to the next in a successive series to accomplish various treatment goals. Thus, the systems and methods of the present invention provide the design, production and use of such multiple stiffness positioning appliances in orthodontic treatment. Similarly, the devices of the present invention provide variable stiffness appliances which may be used independently for purposes other than repositioning, such as for retaining teeth in a desired position. Thus, reference hereinafter to repositioning appliances with portions having differing or varying stiffnesses or hardnesses is not intended to limit the scope of the present invention and is understood to include appliances of the described design for other purposes.

In a first aspect of the present invention, an elastic repositioning appliance may be comprised of portions with differing elastic moduluses. Elastic modulus may be used to express or describe the stiffness of a material or a material's resistance to elastic deformation. Therefore, elastic modulus may be used hereinafter to refer to stiffness. The different portions of the appliances will also usually vary in hardness. More usually, stiffer portions will be harder while the less stiff portions will be softer. Hardness is usually measured as a "durometer" reading on either the A or the D scale. In most instances, the present invention will be more concerned with the elastic modulus of the material since that will effect the force applied to the teeth for either moving the teeth or for gripping or anchoring the teeth. In other instances, however, the hardness of the material may be more important, e.g., to avoid trauma to soft tissue regions engaged by the appliance. The remaining description and claims generally refer to materials having greater and lesser stiffnesses. It will be appreciated that such terminology will also comprise materials having greater and lesser hardnesses.

The elastic modulus of a material is the ratio of the increment of unit stress to an increment of unit deformation within the elastic limit. When a material is deformed within the elastic limit, the bonds between adjacent atoms are stretched but not broken. The magnitude of the elastic modulus is indicative of the atomic and molecular bonding forces. When the stress is relieved, the material returns to its original shape and the deformation is nonpermanent. Different materials may have different elastic moduluses based on their molecular structures. Some materials, such as certain polymers, may be specially produced to have different elastic moduluses while retaining similar chemical compositions (and thus assuring compatibility of the different modulus materials in a single structure). Likewise, the elastic modulus of a polymer or other material may be enhanced or otherwise modified. This may be achieved by adding a powder, such as $CaCO_3$, talc, $TiO_2$, glass, diamond or a polymer powder, to name a few. In addition, this may be achieved by embedding structural reinforcements, such as metal pieces, strips, wires, mesh, lattices, networks, polymeric filaments, or the like. In addition, the elastic modulus may be altered by post-production methods, such as layering, coating, interpenetrating, treating with various chemical agents, and altering the temperature, to name a few. In the resulting appliance, the elastic moduluses of the varying portions will usually range from 0.5 to 5 GigaPascal (GPa), although in some instances portions of the appliance may fall outside of this range. The elastic modulus of one portion may differ from another portion by 25% to 600%, or more.

The differing elastic moduluses of different portions of the dental appliance shells of the present invention will exist while the device is present over teeth in a normal oral environment. Thus, different portions of the appliance shell will impart different forces to the immediately underlying teeth, where the level of the force depends both on the device geometry or tooth positions (relative to the underlying tooth or teeth, which may vary over time) and on the elastic modulus of that portion of the device (which will remain constant over time in the normal oral environment). The present invention should be distinguished from that described in copending application Ser. No. 09/250,962, where the stiffness of a dental appliance shell may change over time by expose to a non-oral environment, such as elevated temperature or changed osmolality. Of course, the dental appliance shells of the present invention which have different portions with differing stiffness may also incorporate regions (including the entire appliance) where a change in stiffness may be induced according to the teachings of application Ser. No. 09/250,962, the full disclosure of which is incorporated herein by reference.

In a first embodiment, portions of the shell of an elastic repositioning appliance may be composed of material(s) which differ in elastic moduluses and/or hardnesses along a mesial-distal axis. A mesial-distal axis may be defined as an axis following the gingival line or dental arch. Thus, the elastic repositioning appliance may be comprised of portions with a lower elastic modulus covering the molars, for example, and portions with a higher elastic modulus covering the remainder of the teeth. In this example, the portions may be relatively large so that a portion may receive one or more teeth, such as contiguous molars. This may be utilized when one or more teeth are to provide an anchor or base region for imparting repositioning force against another tooth or teeth. The portion of the appliance covering the anchor teeth may be of a relatively flexible nature with a lower elastic modulus than the portion covering the teeth to be repositioned. This is because the portions covering the anchor teeth may not need to apply repositioning forces to the teeth they cover; they may merely be designed to hold the appliance in place. Consequently, a high level of rigidity or stiffness may not be required. However, it may be appreciated that portions covering anchor teeth may in fact require a higher stiffness material than other portions, including portions which are designed to apply repositioning forces. Thus, any variation of stiffness or elastic modulus along a mesial-distal axis is included in this embodiment.

The introduction of such portions or regions with more flexibility provides utility in ease of use for the patient. The patient may find ease in positioning the appliance with the more flexible portions first which may guide the appliance in placement of the more rigid, slightly misfit portions designed for repositioning. This sequence may be reversed in removal of the appliance. Likewise, such flexibility may also allow for any slight differences in mold versus appliance versus dentition geometry which may otherwise make placement and removal of the appliance more difficult. In some cases, a generally misfit appliance may "pop off" or have a tendency to disengage even when properly positioned over the teeth. Increased flexibility may reduce these tendencies.

In further embodiments, portions of the elastic repositioning appliance may vary in elastic moduluses along different and/or additional axes. For example, moduluses may vary along a facial-lingual axis. Facial may be defined as next to or toward the lips or cheek, including terms labial and buccal. Lingual may be defined as next to or toward the tongue. Thus, a facial-lingual axis may be described as an axis following a radial or similar line from the tongue toward the lips or cheek and vice versa. Likewise, moduluses may vary along a gingival-crown axis. This may be described as a substantially vertical axis following a line from the top of the crown at the edge of the occlusal surface of a tooth toward the gingival line or root and vice versa. In a preferred embodiment, an appliance may have a portion with a lower elastic modulus covering the occlusal surfaces of the teeth and a portion with a higher elastic modulus covering the remaining surfaces of the teeth. Thus, the moduluses may vary along a facial-lingual axis and/or a gingival-crown axis, depending on the boundaries of the delineated portions. Such a design may incorporate added flexibility to the appliance while maintaining adequate repositioning forces in the most efficient areas.

In addition to varying in stiffness along the axes described above, the appliances of the present invention may vary in stiffness or hardness over the "thickness" of the appliance. Usually, such variations and stiffness over the thickness will be accomplished by layering the device, i.e., with layers of differing stiffnesses or hardnesses being placed successively over the mold used to form the appliances, as described in more detail below. Thus, the appliances may comprise shells having first and second portions, as generally described above, where each of those portions comprise layers in a laminar structure. Usually, at least one of the first and second portions will comprise a continuous layer along the mesial-distal axis. The second and optionally additional layers may also be continuous along the mesial-distal axis, but will often be discontinuous, i.e., broken into two or more segments. Such layered devices can provide a variety of benefits. For example, layers formed from stiffer or harder materials can be used to more firmly engage teeth, while the less stiff or softer layers can be used to provide compliance and greater elasticity. In a particular preferred embodiment, the appliance comprises a discontinuous inner layer and a continuous outer layer. At least a portion of the inner layer is configured to engage individual teeth or groups of teeth and will be stiffer or harder than the outer layer. The outer layer, which is less stiff and therefore more compliant, provides the elasticity to move the teeth relative to one another, while the harder inner layer firmly engages the teeth to provide a better grip or anchor upon the teeth.

It may be appreciated that the elastic modulus of the appliance shells may vary over any number of delineated portions. Such portions may be of any size, shape, thickness, or dimension. Thus, such portions may receive entire teeth or they may be of the size to cover only a portion of a tooth or dental surface. When portions are relatively large, an appliance may be divided into, for example, two to five portions. Portions adjacent to one another differ in elastic moduluses, however not all portions of an appliance may differ from each other, such as in the case of an appliance with portions alternating between two moduluses. When portions are relatively small, an appliance may contain an unlimited number of portions, varying along any axis or combination of axes.

In a second aspect of the present invention, such appliances comprised of portions having differing stiffness may be used independently or in a series with similar or differing devices. When used independently, the appliance may be worn to achieve a specific goal with a single device. For example, the appliance may be used as a "retainer" to hold the teeth in a desired position. Or, the appliance may be used for a specific one-time repositioning movement, such as "finishing" or correcting a slight misalignment. When used in a series, the appliances may comprise a system for repositioning teeth from an initial tooth arrangement to a final tooth arrangement. In this case, a plurality of incremental elastic position adjustment appliances comprising polymeric or other material shells are successively worn by a patient to move teeth from one arrangement to a successive arrangement. Individual appliances may be configured so that their tooth-receiving cavity has a shape or geometry corresponding to an intermediate or end tooth arrangement intended for that appliance. Thus, successive individual appliances may have a shape or geometry differing from that of the immediately prior appliance. According to the present invention, some or all of the individual appliances may also be comprised of a material stiffness differing from the stiffness of the immediately prior appliance. In addition, each individual appliance be comprised of portions with varying stiffnesses. In some cases, of course, individual appliances in the system may not vary in stiffness from prior or successive appliances, but only in geometry. In other cases, individual appliances may vary only in stiffness (and not in geometry) when compared to immediately prior or subsequent appliances. Thus, systems according to the present invention may be comprised of appliances having stiffness varying within the appliance and/or from one appliance to the next in the series.

In a specific embodiment, a system of elastic repositioning appliances may comprise individual appliances having uniform elastic moduluses over their entire tooth contact area where the moduluses will differ among successive appliances used in a course of treatment. The elastic modulus of a given appliance may be chosen to be most suitable for a specific type of tooth movement, such as translating, tipping, root uprighting, rotation, extrusion, intrusion or a combination of these. For example, translation may require 70-120 gm of force, whereas rotation may only require 35-60 gm of force. Therefore, an elastic positioning appliance designed for translating teeth may need to have a higher elastic modulus than one designed for purely rotating teeth. This is again due to the fact that stiffness of the appliance is a critical factor in imparting repositioning force. Consequently, a series of appliances may be produced for a treatment plan in which successive appliances designed for a specific tooth movement may all have substantially similar elastic moduluses. At the point in the treatment plan in which a different type of tooth movement is desired, further appliances designed for the new tooth movement may have substantially similar elastic moduluses to each other but different from the previous appliances. Such a sequence may be repeated at any time or may continue with new moduluses and tooth movements.

In an additional specific embodiment, one or more appliances may be produced with a suitably flexible elastic modulus to receive and resiliently reposition teeth from an unprescribed arrangement to a prescribed arrangement. This might be necessary in cases of lowered patient compliance. If a patient were to remove an appliance for an unintended and/or extended period of a prescribed treatment time, the patient's teeth may move slightly out of the planned tooth progression. When attempting to reapply the appliance, an appliance which is too rigid may not be able to accommodate these slight differences. Thus, a more flexible appliance (but having an identical geometry) may be produced for this purpose and may be incorporated into the treatment plan at any given point in the series of successive appliances. The ability to return to the same geometry is an advantage because it minimizes the need to replan the treatment protocol.

In a third aspect of the present invention, systems for repositioning teeth from an initial tooth arrangement to a successive tooth arrangement comprise a plurality of incremental elastic position adjustment appliances in which at least one appliance has the same shape yet different elastic modulus as an immediately prior appliance. In a specific embodiment, a series of incremental appliances may be produced with differing elastic moduluses to reposition teeth from an initial tooth arrangement to the next successive tooth arrangement in a progression of arrangements to the final arrangement. Each of the appliances in the series from the first to the next successive tooth arrangement may have the same shape or geometry since the tooth movement represents one step in tooth movement. However, the variance in elastic moduluses may allow for a larger step or increment in tooth movement than may be obtainable with consistent, rigid appliances. For example, an appliance may be produced with a tooth arrangement which is substantially misaligned from the initial arrangement. High modulus appliances may not be flexible enough to allow the appliance to fit over the teeth in the initial arrangement. However, a series of appliances of the same shape may be produced with increasing elastic moduluses from relatively low to adequately high. The patient may begin with the lowest elastic modulus appliance which may be the most flexible to fit over the teeth. As the teeth are repositioned, the patient may successively utilize each appliance in increasing modulus until the teeth have conformed to the successive tooth arrangement. At that time, the patient may begin a new series of appliances with varying moduluses and a shape to reposition the teeth to the arrangement of the next step in the repositioning progression. The ability to reduce the number of different appliance geometries required for a single course of treatment can provide a significant reduction in planning effort and manufacturing costs.

In a fourth aspect of the present invention, the elastic modulus of an appliance or portions of an appliance may be modified in a number of different ways. To begin with, the elastic modulus may be determined by the choice of materials. For example, metals will generally have a higher elastic modulus than polymers due to atomic structure. For example, the modulus values for metals may range between 48 and 414 GPa, whereas the modulus for polymers may range from 0.5 to 35 GPa. Thus, it will be possible to form appliances having moduluses which differ greatly by forming different portions from metal(s) and polymer(s), or by forming successive appliances from metals and polymers. Usually, however, the appliances will comprise or consist of a polymeric shell formed from a single polymer, multiple polymers, copolymers, and the like, typically by thermoforming and/or lamination. Stiffness of a polymer may be varied within a range (typically 0.5 GPa to 5 GPa) by changing the molecular structure of the polymer chains. Polymer chains with hindered side-chains are unable to pack as closely as those with smaller side-chains. Thus, such a polymer may have more intermolecular motion and therefore a lower bulk elastic modulus. Stiffness can also be changed by controlling the degree of cross-linking as well as the cross-linking entity within a polymer or copolymer. Further, alternatively, differing elastic moduluses may be created within the same polymer shell by layering or laminating the same or different polymers. Two layers of a polymer material bonded together to form an integral appliance, i.e., an appliance having a monolithic shell structure where the layers are resistant to delamination, may have a higher elastic modulus than a single layer of such material. Thirdly, different elastic moduluses may be created with a single layer of one type of polymer material by production methods, such as coating, treating with various chemical agents, and altering the temperature, to name a few.

Further, different elastic moduluses may be produced by forming selectively reinforced and/or composite-type materials. For example, a polymer material may be reinforced with structures such as strips, wires, pieces, mesh, lattices, networks, and the like. These structures may be comprised of any suitable material, particularly metals and alloys but also including polymer filaments, wires, braids, and the like. Likewise, composite materials may be comprised of interpenetrating polymeric networks. An interpenetrating polymeric network is comprised of a base material and an additional material that interpenetrates the base material to alter its mechanical properties. For example, the base material (A) may be a solid polycarbonate. The added material (B) may be a liquid polymer, monomer or crosslinking agent which is allowed to interpenetrate and activate to form a composite network. The composite (A+B) may have a stiffness which is greater than the sum of its parts, (A) and (B). Further, another material (C) may also be allowed to interpenetrate and activate to form a new composite network. The composite (A+B+C) may also have a stiffness which is greater than the sum of its parts, (A), (B) and (C). With this method, any number of composites may be formed providing a wide range of mechanical properties, specifically stiffnesses. In addition, a number of these production methods may provide materials with gradual changes in elastic moduluses. For example, purposely irregular coating of a polymer material may provide higher stiffness in areas with thicker coating and lower stiffness in areas with thinner coating. This may be applied to a number of production methods.

DESCRIPTION OF THE SPECIFIC EMBODIMENTS

The present invention provides improved devices, systems and methods for incrementally repositioning teeth using a plurality of discrete polymeric appliances of variable flexibility, where each appliance successively repositions one or more of the patient's teeth by relatively small amounts. Flexibility may be defined by elastic modulus of the polymeric material and may vary within a given appliance or may vary throughout a series of appliances according to a prescribed orthodontic treatment plan.

Figure 1:
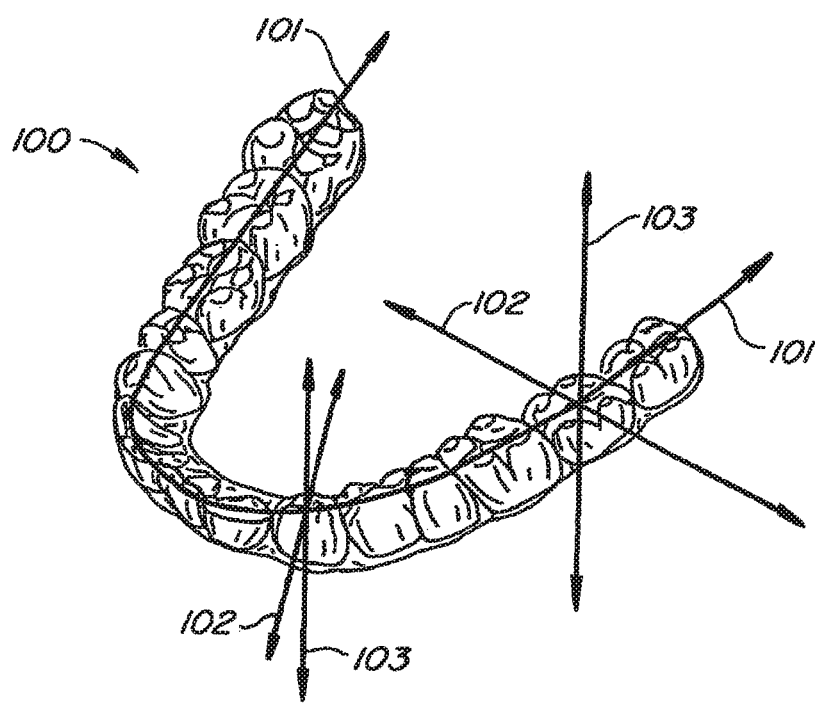
FIG. 1 is a perspective illustration of an embodiment of an appliance of the present invention and descriptive axes.

Referring to FIG. 1, portions of an elastic repositioning appliance 100 may vary in elastic modulus along a mesial-distal axis 101, facial-lingual axis 102, gingival-crown axis 103, or any axis in-between these representative axes. As previously described, a mesial-distal axis may be described as an axis following the gingival line or dental arch, a facial-lingual axis may be described as an axis following a radial or similar line from the tongue area toward the lip or cheek area, and a gingival-crown axis may be described as an axis following a substantially vertical line from the crown of a tooth toward the gingival line or root. Such axes are defined for descriptive purposes and are not intended to limit the scope of the present invention.

Figure 2:
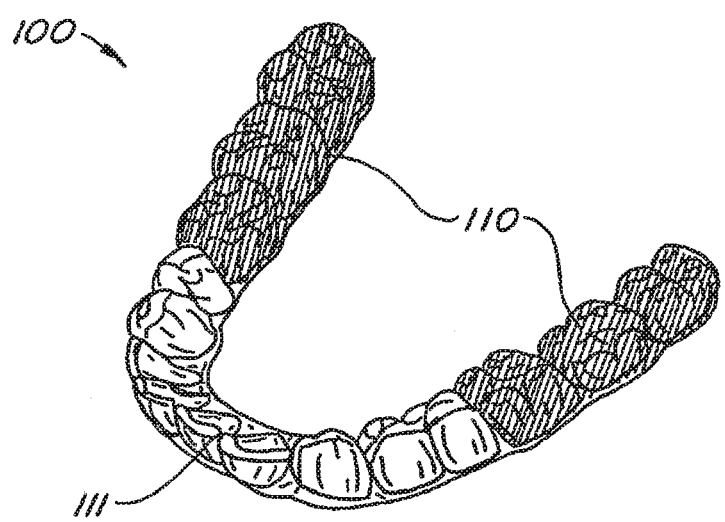
FIG. 2 illustrates an embodiment of an appliance with relatively large portions varying in elastic modulus along a mesial-distal axis.

As shown in FIG. 2, portions of an elastic repositioning appliance 100 may vary in elastic modulus mesial-distally. For illustrative purposes, portions with a lower elastic modulus 110 are shaded to easily distinguish differences in elastic modulus throughout a device. In this example, the appliance 100 may be described as having three portions. Two portions cover contiguous sets of molars and are comprised of an elastomeric material of a lower elastic modulus 110 and are thus shaded. The portion in-between these portions is of a higher elastic modulus 111 and is thus not shaded. All portions in this embodiment are relatively large so that the portions may receive one or more teeth, such as molars, premolars, incisors, and the like. Likewise, nonadjacent portions may have the same elastic modulus, such as the two lower elastic modulus 110 portions, or they may be different from each other while maintaining a difference from the higher elastic modulus 111 portion. In other words, an appliance 100 with three distinct portions may be comprised of two or three elastic moduluses.

Figure 3:
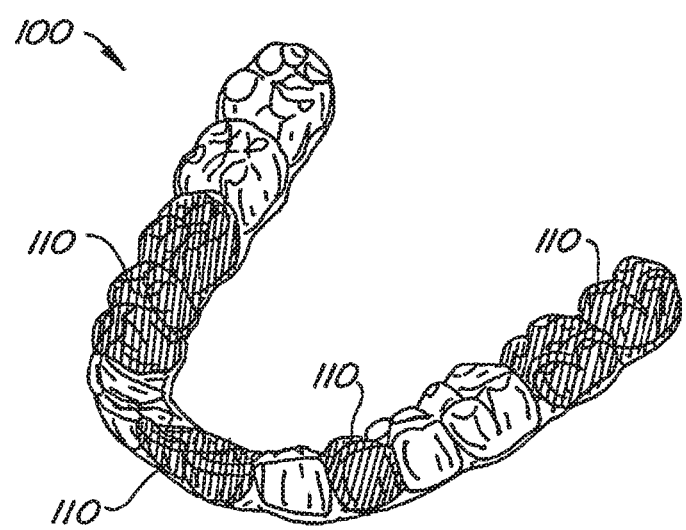
FIG. 3 illustrates an embodiment of an appliance with smaller portions varying in elastic modulus in a non-symmetric pattern along a mesial-distal axis.
Figure 4:
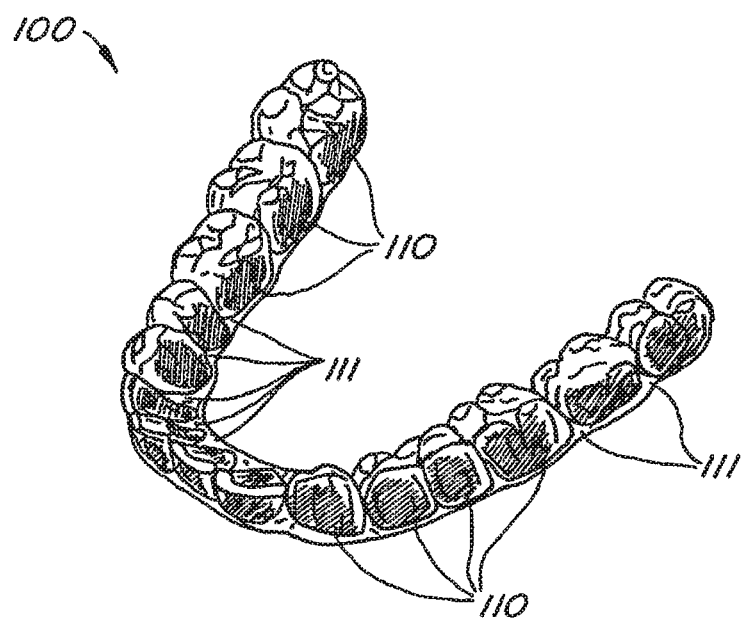
FIG. 4 illustrates an embodiment of an appliance varying in elastic modulus along a mesial-distal axis in which portions covering proximal or interproximal spaces are of differing modulus.

As illustrated in FIG. 3, such portions may not be symmetrical and they may not cover more than one tooth. Portions with a lower elastic modulus 110 may alternate in an uneven fashion along a mesial-distal axis as shown. In addition, adjacent portions may be of a size to cover only a portion of a tooth or dental surface. Referring to FIG. 4, portions of lower elastic modulus 110 may be present covering the facial or lingual surfaces of the teeth, while portions of higher elastic modulus 111 may be present covering the proximal or interproximal spaces. This may be advantageous to provide repositioning forces, such as translation forces, at the most efficient locations for this type of movement. At the same time, flexibility is provided in portions that may be less involved in the application of force, allowing more freedom and comfort for the patient.

Figure 5:
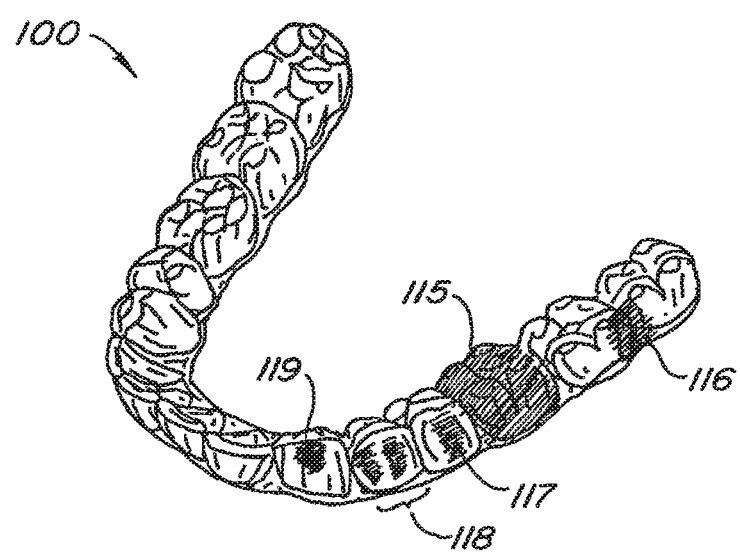
FIG. 5 illustrates a variety of appliance portions varying in elastic modulus along a mesial-distal axis.

Referring to FIG. 5, the elastic modulus of an appliance 100 may vary over any number of delineated portions and may be of any size, shape, thickness or dimension, to name a few. Such portions may be sized to receive an entire tooth 115 or they may be of the size to cover only a portion of a tooth. For example, a portion with a lower elastic modulus 110 may be sized to cover a proximal or interproximal space 116, including portions covering the gingival line. This may be desirable to provide comfort to the gums when wearing the appliance, and also to increase the contact of the appliance with the interproximal regions. In this case, softer, more flexible material may be able to form more closely to the interproximal regions, enabling a higher level of repositioning force to be applied.

Portions may also be sized and arranged to cover part of a facial surface 117, or two or more of such portions may cover part of a facial surface 118, allowing the elastic modulus to vary mesial-distally within a single tooth. Further, the portion may be sized to cover an isolated region of a facial surface 119. Such embodiments are a limited presentation of the possible sizes, configurations, and combinations of varying elastic modulus portions in an appliance 100 of the present invention. Such possibilities may be unlimited.

Figure 6:
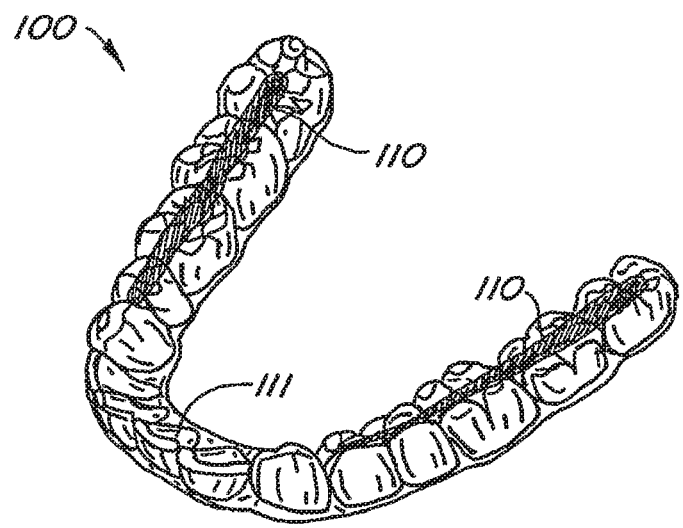
FIG. 6 is a perspective illustration of an embodiment of an appliance varying in elastic modulus along a facial-lingual axis.

As shown in FIG. 6, portions of an elastic repositioning appliance 100 may vary in elastic modulus facial-lingually. In this embodiment, the appliance 100 is shown to have a portion with a lower elastic modulus 110 covering a portion of the occlusal surfaces of the teeth and a portion with a higher elastic modulus 111 covering the remaining surfaces of the teeth. Thus, the elastic modulus varies along a facial-lingual axis. Such a design may be beneficial to provide repositioning forces, such as translation forces, along the proximal and/or interproximal spaces which are the most efficient locations for this type of movement. At the same time, flexibility is provided in portions that may be less involved in the application of force, the occlusal surfaces. This may allow increased freedom and comfort for the patient while maintaining adequate repositioning forces.

Figure 7:
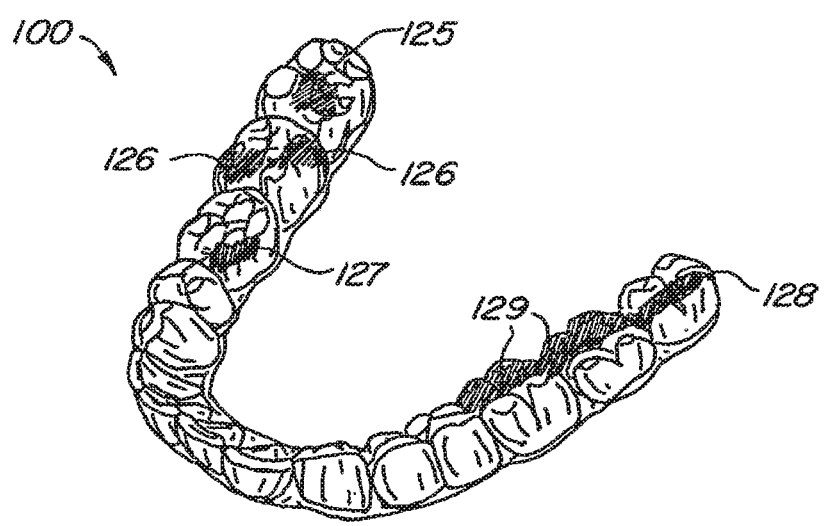
FIG. 7 illustrates a variety of appliance portions varying in elastic modulus along a facial-lingual axis.

Referring to FIG. 7, the elastic modulus of an appliance 100 may again vary over any number of delineated portions and may be of any size, shape, thickness or dimension, to name a few. A portion of lower elastic modulus 110 may be sized to cover only a portion of a tooth. For example, it may cover the center of the occlusal surface 125, alternating cusps or cusp tips 126, or isolated portions of any given cusp or cusp tip 127. Likewise, a portion of lower elastic modulus 110 may be of a larger size to cover, for example, the outside margin or buccal cusps of a tooth 128 or the inside margin or lingual cusps of a contiguous grouping of teeth 129. As before, such embodiments are a limited presentation of the possible sizes, configurations, and combinations of varying elastic modulus portions in an appliance 100 of the present invention. Such possibilities may be unlimited.

Figure 8:
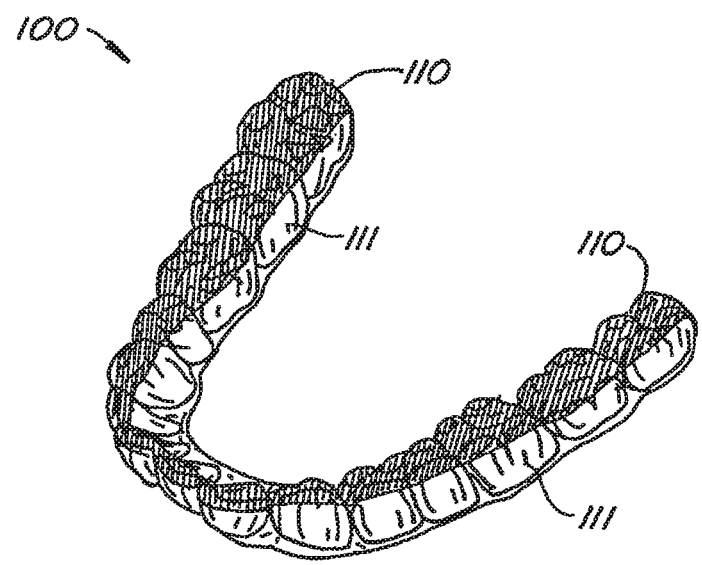
FIG. 8 is a perspective illustration of an embodiment of an appliance varying in elastic modulus along a gingival-crown axis.

As shown in FIG. 8, portions of an elastic repositioning appliance 100 may vary in elastic modulus crown-gingivally. In this embodiment, the appliance 100 is shown to have a portion with a lower elastic modulus 110 covering the occlusal surfaces of the teeth and a portion with a higher elastic modulus 111 covering the remaining surfaces of the teeth. This is a modified representation of the embodiment depicted in FIG. 6 in which the portion of lower elastic modulus 110 partially covered a portion of the occlusal surfaces. In this embodiment, the occlusal surface is substantially covered with the lower elastic modulus 110 material, therefore it may be considered to be uniform, non-variable, along a facial-lingual axis. It may be more properly described as varying along a gingival-crown axis, as the lower elastic modulus 110 portion may extend over the cusps of the tooth crowns. Thus, the lower elastic modulus 110 material may be seen as being located at the tip of the crown region and vary to a higher elastic modulus 111 material toward the gingival line or margin. In addition, a higher elastic modulus 111 material along the gingival line or margin may improve retention of the device on the teeth. This may also reduce the need for attachment devices to aid in retention. A full description of exemplary attachment devices and methods for a dental appliance is described in co-pending application Ser. No. 09/454,278, incorporated by reference for all purposes and assigned to the assignee of the present inventor. However, such modulus differences are presented only for descriptive purposes and such portions may vary over one or many axes simultaneously or in isolated regions of an appliance 100.

It may be appreciated that the advantages offered by a lower elastic modulus along the occlusional surfaces, as depicted in FIG. 6 and FIG. 8, may be further increased by removing the material from the shell in these areas. Removal of material may form a window such that when the shell is positioned over the patient's teeth, portions of the teeth beneath the window may be exposed. In a preferred embodiment, a polymeric shell may have a plurality of windows over portions of the occlusal surfaces of the teeth. In this case, segments of the shell may still be present along the facial and lingual surfaces of the teeth and across the interdental regions or spaces between the teeth. Exposure of the occlusal surfaces in appropriate size and location may allow interdigitation of the upper and lower teeth. This may also be achieved with the presence of one or a few larger windows over portions of the occlusal surfaces of the teeth. In these cases, segments of the shell may not be present across the interdental regions or spaces between the teeth. In either case, interdigitation of at least portions of the upper and lower teeth may benefit tooth and jaw orientations, leading to improved treatment, appearance, comfort and consequently patient compliance. Thus, such windows may provide the benefits offered by a lower elastic modulus, such that the lowest stiffness may be provided by the absence of the material, while providing additional benefits described above. A full description is provided in U.S. patent application Ser. No. 09/616,222, assigned to the assignee of the present invention.

Figure 9:
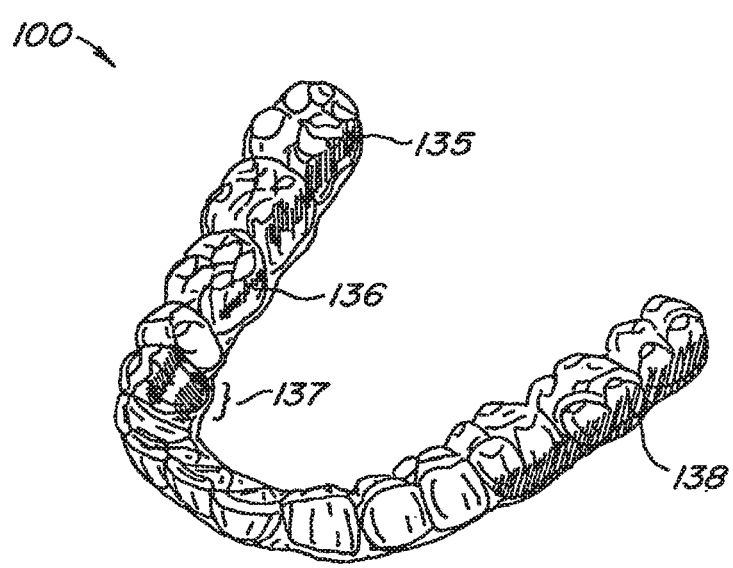
FIG. 9 illustrates a variety of appliance portions varying in elastic modulus along a gingival-crown axis.

Referring to FIG. 9, the elastic modulus of an appliance 100 may again vary over any number of delineated portions and may be of any size, shape, thickness or dimension, to name a few. A portion of lower elastic modulus 110 may be sized to cover only a portion of a tooth along this axis. For example, it may cover the upper portion of the lingual surfaces near the cusps of the crown 135, or a midway "stripe" through the lingual surface of a tooth 136. Likewise, it may be sized so that more than one "stripe" may cover the surface of a tooth 137, as in the case of a portion at the gingival margin and a portion near the cusps of the crown. Similarly, a portion of lower modulus may be sized so that it covers a contiguous grouping of teeth, such as the buccal surfaces along the gingival margin 138. As before, such embodiments are a limited presentation of the possible sizes, configurations, and combinations of varying elastic modulus portions in an appliance 100 of the present invention. Such possibilities may be unlimited.

Figure 10:
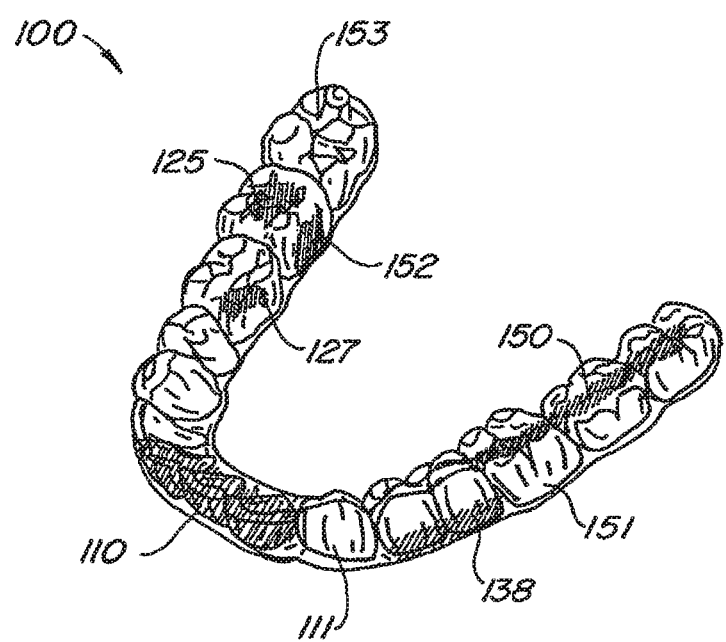
FIG. 10 illustrates a variety of appliance portions varying in elastic modulus along one or more described axes.

As illustrated in FIG. 10, variance in elastic modulus in relation to size, shape, location, orientation, and axis, as described above, may be combined in a single appliance 100 to provide an unlimited variety of appliance 100 designs and constructions. In this example, portions of the appliance 100 vary mesial-distally, such as by comparing the lower elastic modulus 110 portion covering a group of incisors with the higher elastic modulus 111 portion covering the canine tooth. Portions may also vary facial-lingually, as depicted by the partial covering of the occlusal surfaces of the molars 150 or the isolated portion of a given cusp or cusp tip 127. Likewise, portions may vary crown-gingivally, such as the portions covering the buccal surfaces along the gingival margin 138. These portions also vary mesial-distally creating a compound variance, as portions adjacent to these areas are not identical, as in comparison of portions covering the buccal surfaces along the gingival margin 138 with the adjacent tooth 151 having partial covering of the occlusal surface of the molar 150. Portions may also vary along the three major axes simultaneously. This can be seen in the portion covering the center of an occlusal surface 125, which varies facial-lingually, the lingual face of a molar along the gingival margin 152, which varies crown-gingivally, and the adjacent uniformly covered molar 153, which varies mesial-distally in relation to the previous portions.

According to the present invention, systems for repositioning teeth from an initial tooth arrangement to a final tooth arrangement may be comprised of a plurality of incremental elastic position adjustment appliances with varying elastic moduluses. Thus, in addition to combined variances in a given appliance 100, as described above, a plurality of such appliances 100 with differing patterns of elastic modulus variance may be used in a system for repositioning teeth throughout a sequence of tooth arrangements. This may be illustrated by FIGS. 2-10 with differing tooth geometries, viewed as a series of appliances 100 for a single treatment plan.

Figure 11:
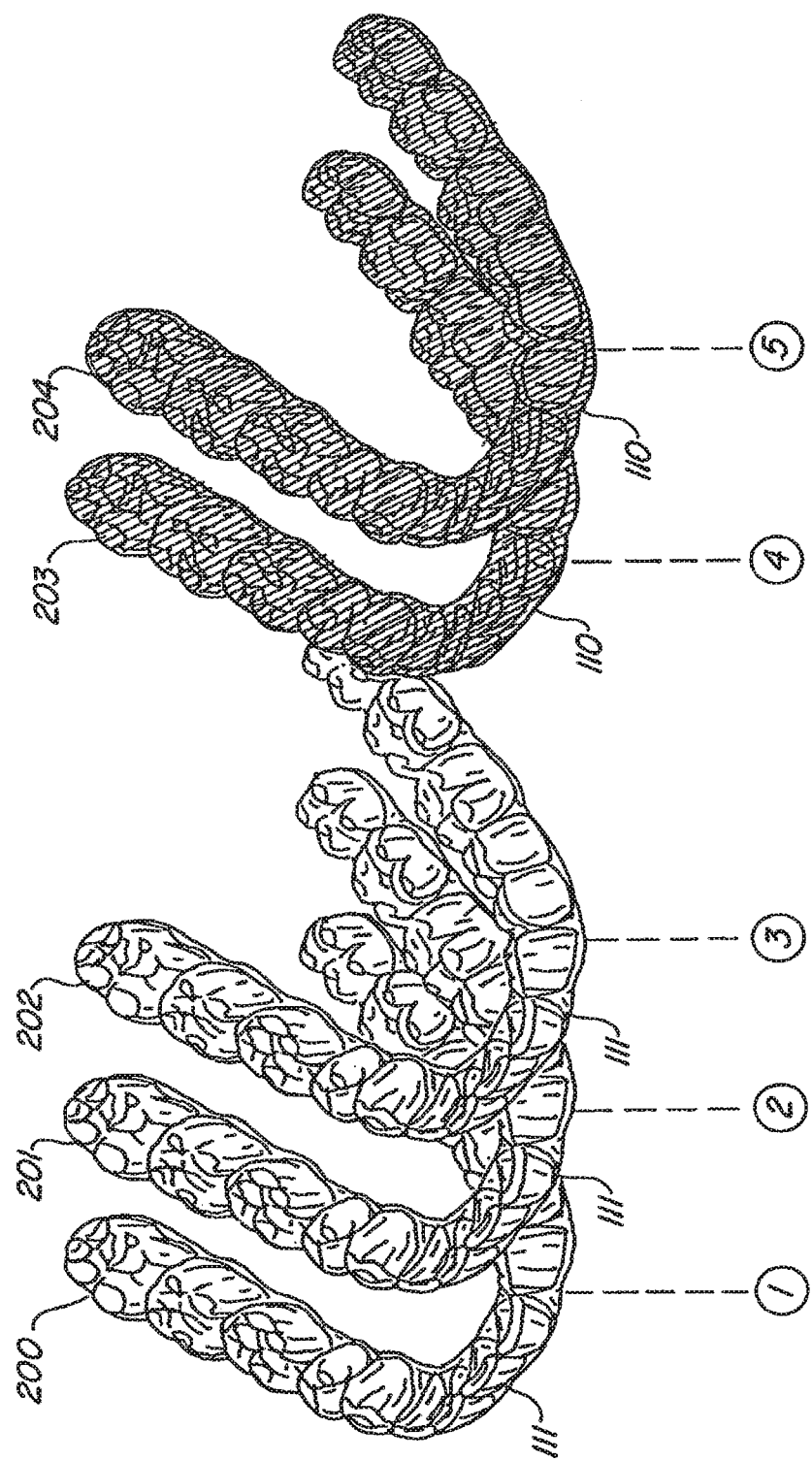
FIG. 11 depicts a series of appliances differing in elastic modulus at specific intervals throughout a treatment plan.

Alternatively, as shown in FIG. 11, the polymeric shells of the appliances 100 may have uniform elastic moduluses over their entire tooth contact area. In this depiction, each appliance 100 differs in shape or tooth geometry and represents a stage in the overall treatment plan. Thus, five stages are depicted, as there are five appliances 100 shown. The first three appliances 200, 201, and 202, respectively, may have a uniform elastic modulus chosen for a specific type of tooth movement. For example, appliances 200, 201 and 202 may be designed for pure translation, requiring a relatively high elastic modulus 111. Thus, the appliances are not shaded in the illustration. At stage 4, a different type of tooth movement, such as tipping, may be desired requiring a lower elastic modulus 110. Therefore, appliances 203 and 204 may continue the series of differing shape or tooth geometries to create such movements, but the elastic modulus may differ from the prior appliances, 200, 201, and 202. Thus, these appliances are shaded in the illustration. The remainder of the treatment plan may feature a similar series of appliances, including appliances with uniform elastic moduluses which differ from the appliances immediately prior and/or any appliances previously presented in the series. Likewise, such a series may also include appliances with combined variances, as described above.

Figure 12:
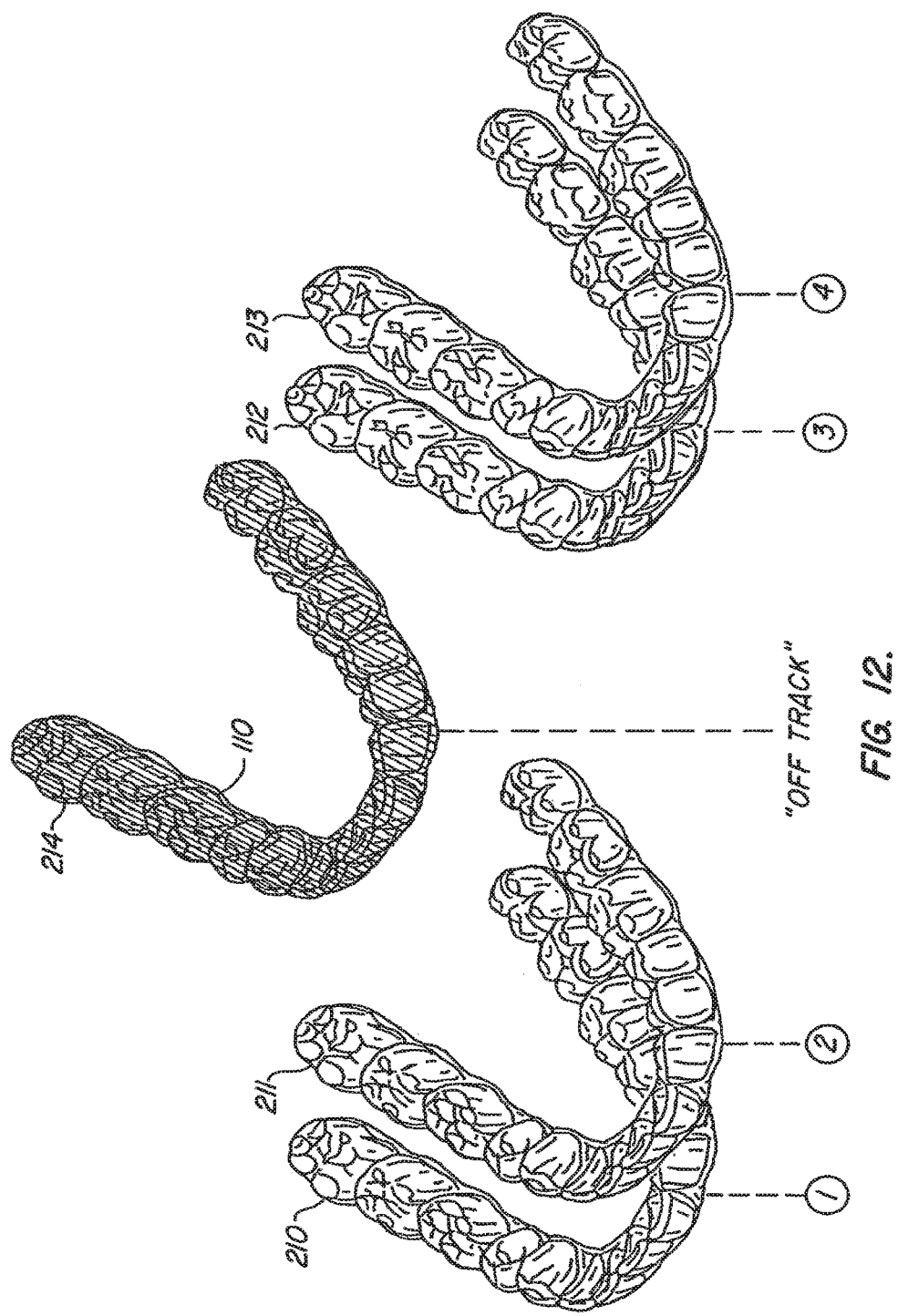
FIG. 12 illustrates the use of an "off track" appliance in a prescribed treatment plan.

Similarly, as shown in FIG. 12, a treatment plan may be prescribed with a series of appliances 100 differing in shape or tooth geometry, of which four stages are depicted, 210, 211, 212 and 213. Such appliances may have any given elastic modulus that is suitable for the prescribed function. Likewise, such appliances may have internal variance in elastic modulus, described previously, or may vary wholly from appliance to appliance throughout the prescribed treatment plan. However, if a patient were to discontinue usage of an appliance for an unprescribed period of treatment time, such as between stages two (appliance 211) and three (appliance 212) depicted in FIG. 12, the patient's teeth may move slightly out of the planned tooth arrangement. Such a patient may be considered "off track" in which their current tooth arrangement has diverted from the series of projected tooth arrangements, creating an unprescribed tooth arrangement. When attempting to apply the next successive appliance 212, it may be too rigid to accommodate these slight differences. Therefore, a new more flexible appliance 214 may be produced for this purpose and may be incorporated into the treatment plan. Such an appliance 214 may have the same shape or tooth geometry as the next successive appliance 212, but it may have a lower elastic modulus 110, depicted by shading. The increased flexibility may allow the appliance 214 to conform to the unprescribed arrangement and reposition the teeth toward an arrangement that the next successive appliance 212 may therefore fit. Such an appliance 214 may be used at any point in the series of successive appliances.

Figure 13:
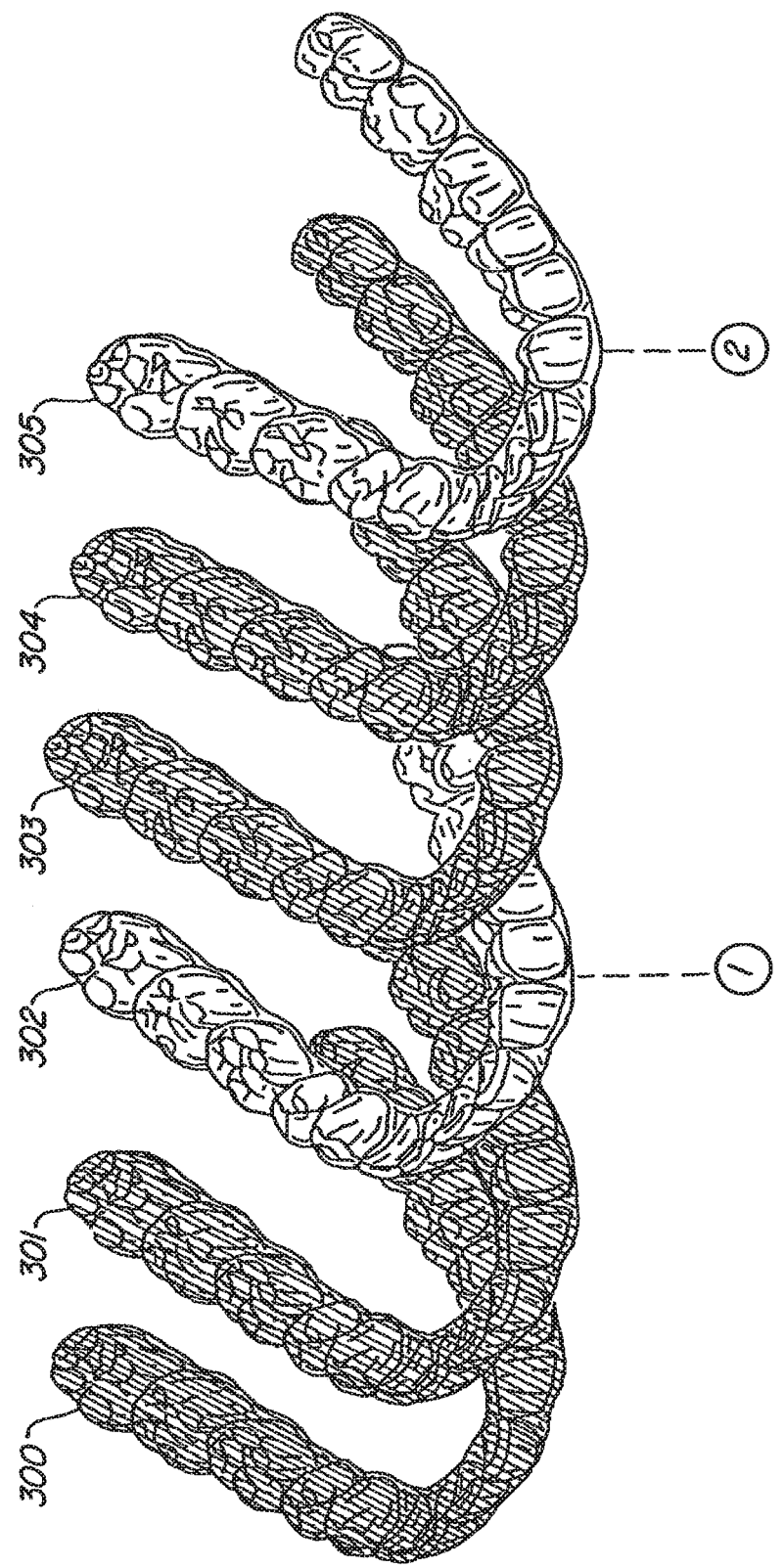
FIG. 13 illustrates the use of a series of appliances with gradually increasing elastic moduluses and similar or identical geometry in a series of intervals throughout a treatment plan.

As shown in FIG. 13, a series of incremental appliances, 300, 301, 302, 303, 304 and 305, may be produced with differing elastic moduluses, illustrated by variation in shading, to reposition teeth from an initial tooth arrangement to the next successive tooth arrangement in a progression of arrangements to the final arrangement. FIG. 13 illustrates two steps in such a progression. A step or stage represents a change in shape or geometry of an appliance 100 to reposition the teeth into the next prescribed arrangement in a series. Therefore, appliances 300, 301, and 302 represent the first stage and have one shape and 303, 304, and 305 represent the second stage and have a differing shape. The appliances 300, 301, and 302 representing the first stage may vary in elastic moduluses from more flexible (appliance 300) to more rigid (appliance 302). The patient may begin the treatment sequence with the more flexible appliance 300 of the first stage. Such flexibility may allow an appliance with a substantially misaligned geometry to fit over the patient's teeth and apply repositioning forces. As the teeth gradually move toward the desired arrangement, the patient may progress to the next appliance 301 in the first stage. This appliance 301 may be more rigid than the prior appliance 300. The patient may continue through any number of appliances throughout a stage. Upon completion of the stage, the patient may repeat the process in stage two, beginning with the more flexible appliance 303 and culminating with the more rigid appliance 305. The patient may then continue through any number of stages to the endpoint of treatment.

Such a system may provide a number of benefits. First, the variance in elastic modulus throughout each step may allow for a larger step or increment in tooth movement between each step than may be obtainable with consistent, rigid appliances. Such flexibility may allow the appliance to fit over a tooth arrangement that is more misaligned while the increase in rigidity throughout each stage may provide sufficient repositioning forces which may not be obtainable with highly flexible appliances. These larger steps require fewer appliances in a series to have a change in shape or geometry. Consequently, fewer molds may be required to form such appliances, which lowers cost and treatment time for the patient. In addition, if the patient were to become "off track" by suspending treatment, it may be possible for the patient to resume the prescribed treatment plan by reentering treatment at the start of the step or stage in which the patient previously aborted. This appliance may be flexible enough to fit over the teeth in the unprescribed arrangement and gradually reposition the teeth throughout the stage as originally prescribed. This may also reduce cost and treatment time since the production and fitting of a flexible "off track" appliance, as illustrated in FIG. 12, may be avoided.

The elastic modulus of an appliance or portions of an appliance of the present invention may be determined by a number of design features, methods, materials and similar means. In a preferred embodiment, the appliance may be comprised of a polymeric shell which is heat formed over a mold of a patient's dentition. This is typically accomplished by heating a thermoformable polymer material and applying vacuum or pressure to form the polymer to the mold. Alternatively, reaction casting may be used to produce such an appliance. Hereinafter, description will pertain to thermoforming, however such concepts and techniques may be equally applied to reaction casting or similar methods and are not to limit the scope of the invention.

Figure 14:
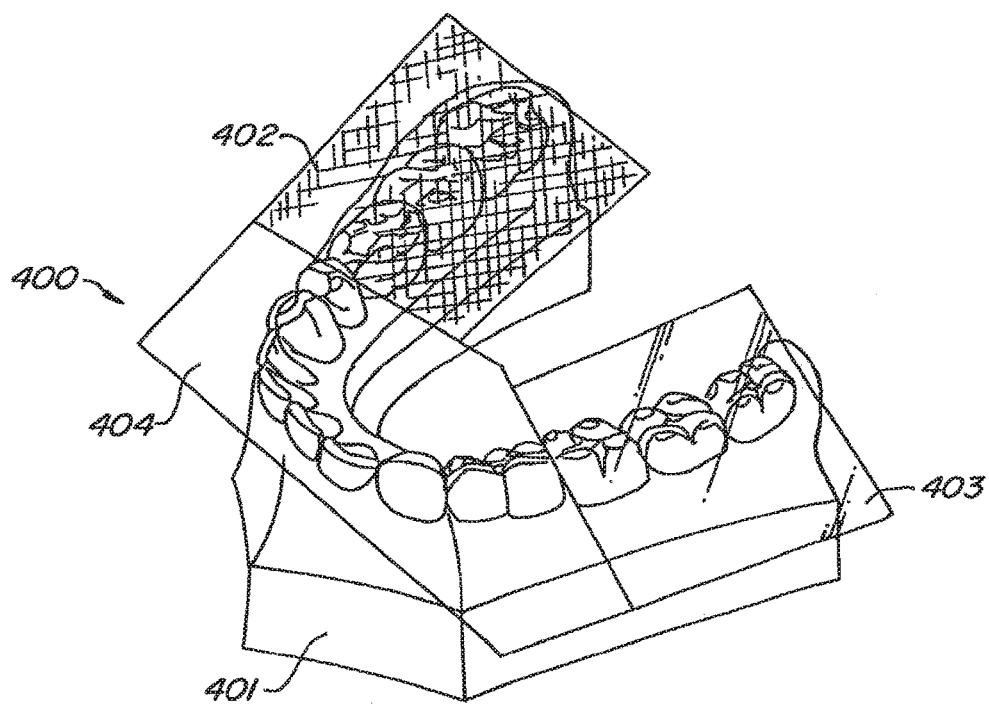
FIG. 14 illustrates a method of fabricating a multi-modulus appliance.

To produce an appliance with uniform elastic modulus, a polymer sheet with a specific elastic modulus and thickness may be thermoformed over a mold and trimmed for patient use. Appliances with differing uniform elastic moduluses may be produced by altering one or more of three variables: 1) polymer type, 2) elastic modulus, 3) thickness. To produce an appliance with portions of differing elastic moduluses, a number of techniques may be utilized. Referring to FIG. 14, portions of polymer sheeting 400 may be positioned over a mold 401 in designated areas and thermoformed together into a final polymeric appliance. Each portion of sheeting 400 may be chosen based on the three above mentioned variables to provide a desired elastic modulus. Each portion of sheeting 400 may then be positioned in the desired location for elastic modulus changes throughout the finished appliance. In FIG. 14, three portions are presented, a first sheet 402 placed over the right side molars, a second sheet 403 placed over the left side molars and a third sheet 404 placed over the remainder of the teeth. Sheets 402 and 403 are depicted as having differing elastic moduluses to each other and to sheet 404, as shown by shading gradations, however such sheets 402, 403, may be identical. After thermoforming, a finished appliance may appear as that illustrated in FIG. 2.

Figure 15:
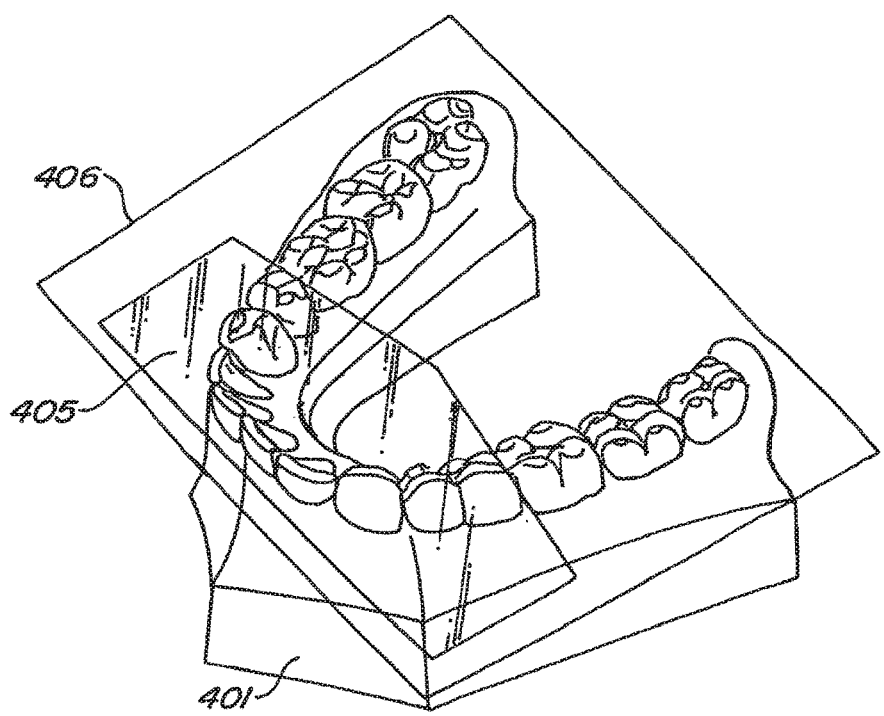
FIG. 15 illustrates a method of layering to fabricate a multi-modulus appliance.

In addition, portions with differing elastic moduluses may be created with the same polymer or different polymers material by layering. Two layers of a polymer material bonded together may have a higher or elastic modulus than a single layer of such material. As illustrated in FIG. 15, a first sheet 405 may be placed over the incisors, canines and premolars of the mold 401 and a second sheet 406 may be placed over the entire dentition. Each sheet may be the same or may differ in terms of any or all of the above mentioned variables. After thermoforming, a finished appliance may also appear as that illustrated in FIG. 2. In this case, the shell covering the molars is comprised of one layer and the remainder of the appliance is comprised of two layers formed into an integral appliance structure. Therefore, the portions covering the molars may have a lower elastic modulus, depending on the combination of materials, than the remaining portion. However, it is possible that a multi-layered structure may have a lower elastic modulus than a single layered structure depending on the above mentioned variables. Thus, it may be appreciated that the described layering technique may provide a variety of moduluses and those stated examples are not intended to limit the scope of the invention.

Figure 16:
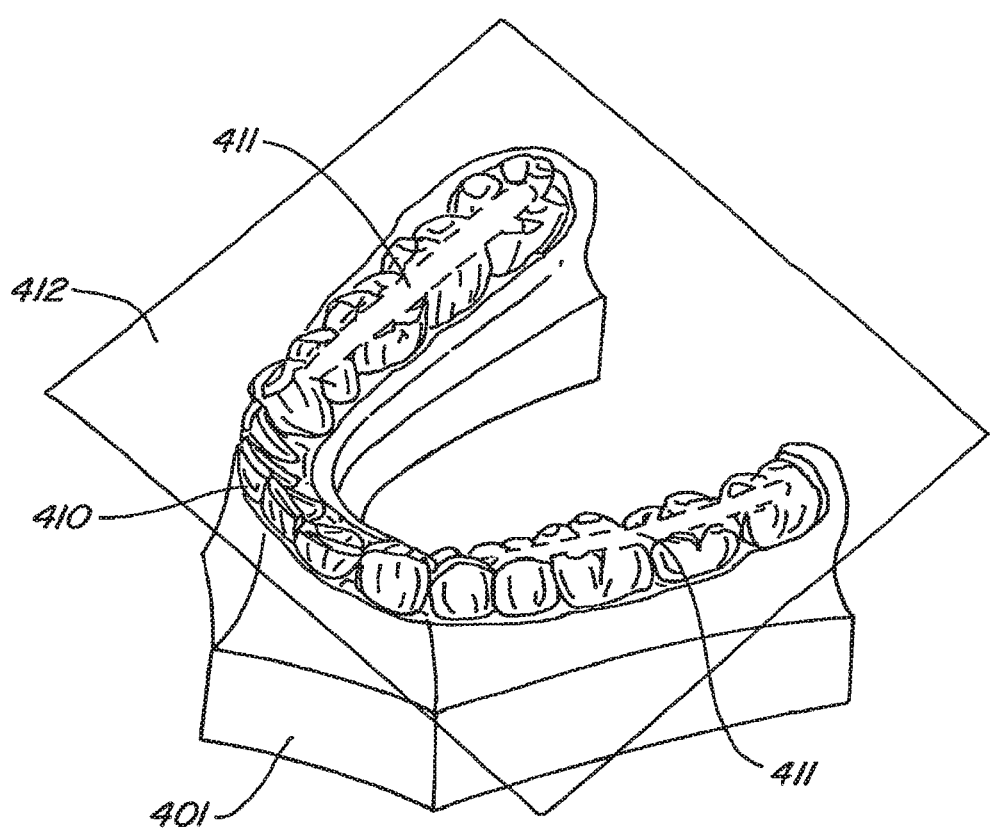
FIG. 16 illustrates an additional method of layering to fabricate a multi-modulus appliance.

Similarly, portions with different elastic moduluses may be created by a multi-step process of layering. Referring to FIG. 16, a first sheet may be thermoformed over the entire dentition of a mold 401 to form a base appliance 410. Portions desired to be of a differing elastic modulus 411, demarcated by a dashed line, may be cut and removed from the formed base appliance 410. A second sheet 412 may then be thermoformed over the entire dentition. This may result in a single layer of material in the portion of differing elastic modulus 411 and a double layer of material in the remaining areas.

It may be appreciated that appliances with differing and gradually changing elastic moduluses may be created by any number of production methods. For example, a base appliance 410 may be coated in a specific area with one or more polymer solutions to "build up" a portion of the appliance for localized rigidity. Such a build-up may also be gradual for a more gradual increase in rigidity. Likewise, a base appliance 410 may be treated in specific areas with various chemical agents to either increase or reduce localized rigidity. This may also include treatments involving temperature changes and other phase altering methods. Similarly, such methods may be combined, including any or all of the above described methods. Likewise, such methods may be utilized for appliances of uniform elastic modulus.

Figure 17:
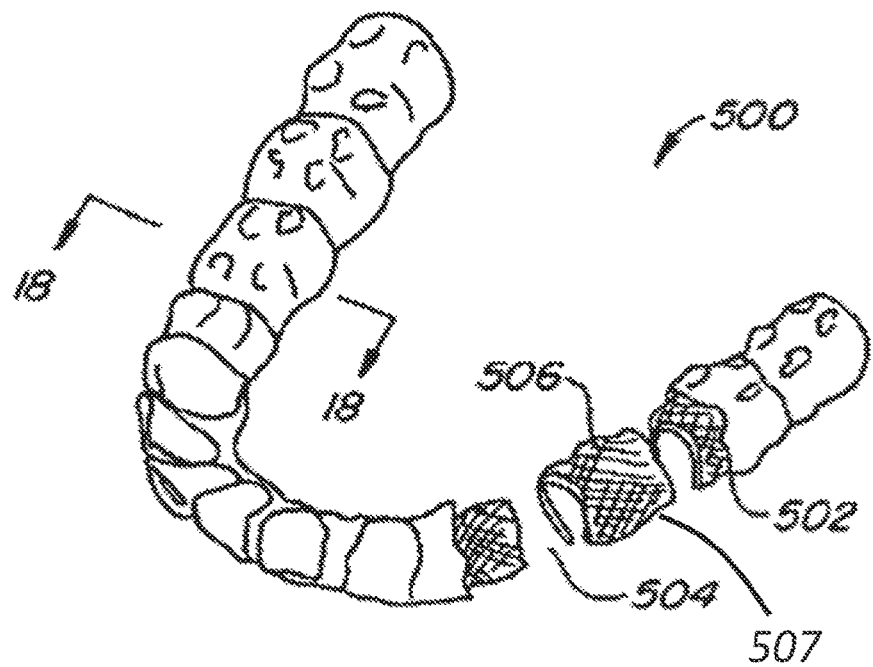
FIG. 17 illustrates an exemplary layered appliance according to the present invention with portions broken away.
Figure 18:
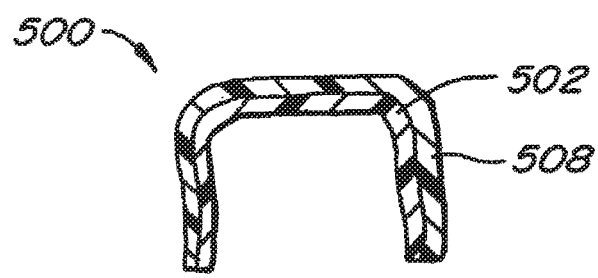
FIG. 18 is a cross-sectional view taken along line 18-18 of FIG. 17.

The fabrication process illustrated in FIG. 16 may be used to prepare a preferred laminated appliance structure 500, as illustrated in FIGS. 17 and 18. An inner layer 502 is formed from a relatively stiff polymeric material and molded over a positive tooth model which represents the desired appliance geometry. After the layer 502 is formed, it can be segmented into two or more sections which conform to individual teeth or groups of teeth when the appliance is placed over the patient's jaw. As shown in FIG. 17, gaps 504 may be formed between individual sections 506, each of which conform to and receive an individual tooth or group of teeth. An outer layer 508 is continuous in the mesial-distal axis and covers all the segments 506 of the inner layer 502. By providing an inner layer 502 having a higher stiffness, firm gripping or anchoring of the underlying teeth can be achieved. Moreover, by providing an outer layer 508 which is less stiff or more compliant, ease of removing and replacing the appliance can be significantly improved. Moreover, the stiffness or anchoring force can be enhanced without having to concurrently modify the overall or effective elasticity of the appliance which can be selected based on the clinical requirements of moving teeth. That is, the elasticity of the outer layer can be selected to provide an appropriate tooth movement force while that of the inner layer can be chosen to enhance seating characteristics over the teeth. In a specific embodiment, the compliance of the outer layer 508 could be varied along the mesial-distal axis in order to provide for differing forces on the teeth, as discussed generally above.

Although the foregoing invention has been described in some detail by way of illustration and example, for purposes of clarity of understanding, it will be obvious that various alternatives, modifications and equivalents may be used and the above description should not be taken as limiting in scope of the invention which is defined by the appended claims.

What is claimed is:

1. A method for producing an orthodontic appliance, the method comprising:
    providing a mold of patient's dentition;
    forming a first material layer over the mold;
    removing one or more portions of the first material layer after forming the first material layer to form a remaining portion and one or more removed portions of the first material layer, at least one of the one or more removed portions spanning a group of two or more teeth of the patient's dentition; and
    forming a second material layer over the remaining portion of the first material layer so as to produce the orthodontic appliance.

2. The method of claim 1, wherein the second material layer spans the entirety of the patient's dentition and the remaining portion of the first material layer spans less than the entirety of the patient's dentition after removing the one or more portions.

3. The method of claim 1, wherein the remaining portion of the first material layer forms an inner layer of the orthodontic appliance and the second material layer forms an outer layer of the orthodontic appliance.

4. The method of claim 3, wherein an overlapping portion comprises a stiffness greater than a stiffness of the first material layer and a stiffness of the second material layer, the overlapping portion comprising a portion of the first material layer and a portion of the second material layer where the first material layer overlaps a portion of the second material layer.

5. The method of claim 3, wherein an elastic modulus of an overlapping portion is greater than an elastic modulus of a non-overlapping portion, the overlapping portion comprising a portion of the first material layer and a portion of the second material layer where the first material layer overlaps a portion of the second material layer.

6. The method of claim 1, wherein the first material layer differs from the second material layer with respect to one or more of the following: elastic modulus, polymer type, or thickness.

7. The method of claim 1, wherein the first material layer is the same as the second material layer with respect to one or more of the following: elastic modulus, polymer type, or thickness.

8. The method of claim 1, wherein the first material layer has a greater stiffness than the second material layer.

9. The method of claim 1, wherein the orthodontic appliance varies in stiffness along one or more of a mesial-distal axis, a facial-lingual axis, or a gingival-crown axis.

10. The method of claim 1, wherein the orthodontic appliance comprises an occlusal surface having a lower stiffness than the remaining surfaces of the orthodontic appliance.

11. The method of claim 1, wherein the second material layer is continuous along a mesial-distal axis, and wherein the formed first material layer is discontinuous along the mesial-distal axis.

12. The method of claim 1, wherein at least one of the removed one or more portions is sized to cover only a portion of a tooth of the patient's dentition.

13. The method of claim 1, wherein at least one of the removed one or more portions is sized to span a gingival line of the patient's dentition.

14. The method of claim 1, wherein removing the one or more portions comprises segmenting the first layer into a plurality of sections each shaped to receive one or more of the patient's teeth.

15. The method of claim 1, wherein the orthodontic appliance comprises one or more gaps formed between two or more remaining portions.

16. The method of claim 1, wherein the mold comprises a positive model of the patient's dentition in a desired tooth arrangement.

17. The method of claim 1, wherein forming the first material layer comprises thermoforming the first material layer over the mold and forming the second material layer comprises thermoforming the second material layer together with the first material layer.

18. The method of claim 1, further comprising trimming the orthodontic appliance for patient use.

* * * * *